(12) United States Patent
Pashine et al.

(10) Patent No.: US 10,968,279 B2
(45) Date of Patent: Apr. 6, 2021

(54) TL1A ANTIBODIES AND USES THEREOF

(71) Applicant: BRISTOL-MYERS SQUIBB COMPANY, Princeton, NJ (US)

(72) Inventors: Achal Pashine, Mahwah, NJ (US); Guodong Chen, East Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 181 days.

(21) Appl. No.: 16/097,630

(22) PCT Filed: May 5, 2017

(86) PCT No.: PCT/US2017/031281
§ 371 (c)(1),
(2) Date: Oct. 30, 2018

(87) PCT Pub. No.: WO2017/196663
PCT Pub. Date: Nov. 16, 2017

(65) Prior Publication Data
US 2019/0135928 A1    May 9, 2019

Related U.S. Application Data

(60) Provisional application No. 62/333,470, filed on May 9, 2016.

(51) Int. Cl.
*C07K 16/18* (2006.01)
*C12N 5/10* (2006.01)
(Continued)

(52) U.S. Cl.
CPC ........ *C07K 16/2875* (2013.01); *C07K 16/241* (2013.01); *A61K 2039/505* (2013.01); *C07K 2317/21* (2013.01); *C07K 2317/33* (2013.01); *C07K 2317/34* (2013.01); *C07K 2317/76* (2013.01); *C07K 2317/94* (2013.01)

(58) Field of Classification Search
None
See application file for complete search history.

(56) References Cited

U.S. PATENT DOCUMENTS 4,399,216 A    8/1983    Axel et al.
4,439,196 A    3/1984    Higuchi
(Continued)

FOREIGN PATENT DOCUMENTS

EP    338841 A1    10/1989
WO    WO1987004462 A1    7/1987
(Continued)

OTHER PUBLICATIONS

Ladner, R. C., Mapping epitopes of antibodies, Biotechnol. Genet. Eng. Rev. 24:1-30, 2007.*
(Continued)

*Primary Examiner* — Claire Kaufman
(74) *Attorney, Agent, or Firm* — Xiangyu Liu; Nickki Parlet

(57) ABSTRACT

Disclosed are antibodies that bind specifically to the receptor TNF superfamily member 15 (TNFSF15), also known as TL1A. Methods of making and using the anti-TL1A antibodies are also described.

12 Claims, 17 Drawing Sheets

Specification includes a Sequence Listing.

(51) Int. Cl.
| | |
|---|---|
| *C12N 15/10* | (2006.01) |
| *G01N 33/53* | (2006.01) |
| *C07K 16/28* | (2006.01) |
| *C07K 16/24* | (2006.01) |
| *A61K 39/00* | (2006.01) |

(56) References Cited

U.S. PATENT DOCUMENTS

| | | | |
|---|---|---|---|
| 4,447,224 | A | 5/1984 | DeCant, Jr. et al. |
| 4,447,233 | A | 5/1984 | Mayfield |
| 4,486,194 | A | 12/1984 | Ferrara |
| 4,487,603 | A | 12/1984 | Harris |
| 4,596,556 | A | 6/1986 | Morrow et al. |
| 4,634,665 | A | 1/1987 | Axel et al. |
| 4,790,824 | A | 12/1988 | Morrow et al. |
| 4,816,567 | A | 3/1989 | Cabilly et al. |
| 4,941,880 | A | 7/1990 | Burns |
| 5,064,413 | A | 11/1991 | McKinnon et al. |
| 5,179,017 | A | 1/1993 | Axel et al. |
| 5,223,409 | A | 6/1993 | Ladner et al. |
| 5,225,539 | A | 7/1993 | Winter |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,403,484 | A | 4/1995 | Ladner et al. |
| 5,427,908 | A | 6/1995 | Dower et al. |
| 5,476,996 | A | 12/1995 | Wilson et al. |
| 5,530,101 | A | 6/1996 | Queen et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,661,016 | A | 8/1997 | Lonberg et al. |
| 5,693,762 | A | 12/1997 | Queen et al. |
| 5,698,767 | A | 12/1997 | Wilson et al. |
| 5,714,350 | A | 2/1998 | Co et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 5,885,793 | A | 3/1999 | Griffiths et al. |
| 5,939,598 | A | 8/1999 | Kucherlapati et al. |
| 5,969,108 | A | 10/1999 | McCafferty et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,172,198 | B1 | 1/2001 | Sinosich |
| 6,180,370 | B1 | 1/2001 | Queen et al. |
| 6,194,551 | B1 | 2/2001 | Idusogie et al. |
| 6,277,375 | B1 | 8/2001 | Ward |
| 6,521,404 | B1 | 2/2003 | Griffiths et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Grigg et al. |
| 6,737,056 | B1 | 5/2004 | Presta |
| 7,317,091 | B2 | 1/2008 | Lazar et al. |
| 8,101,720 | B2 | 1/2012 | Lazar et al. |
| 9,683,998 | B2 * | 6/2017 | Arch ............... A61P 27/14 |
| 10,626,180 | B2 * | 4/2020 | McGovern ......... G01N 33/6863 |
| 2003/0153043 | A1 | 8/2003 | Carr et al. |
| 2004/0014194 | A1 | 1/2004 | Beyer et al. |
| 2007/0148167 | A1 | 6/2007 | Strohl |
| 2010/0069614 | A1 | 3/2010 | Houtzager et al. |
| 2011/0217310 | A1 | 9/2011 | Siegel |
| 2012/0070861 | A1 | 3/2012 | Macdonald et al. |
| 2012/0073004 | A1 | 3/2012 | MacDonald et al. |
| 2012/0079611 | A1 | 3/2012 | Shih et al. |
| 2012/0114654 | A1 | 5/2012 | Classon et al. |
| 2014/0255302 | A1 * | 9/2014 | Poulton ............... A61P 29/00 424/1.49 |

FOREIGN PATENT DOCUMENTS

| | | |
|---|---|---|
| WO | WO198807089 A1 | 9/1988 |
| WO | WO1989001036 A1 | 2/1989 |
| WO | WO1992003918 A1 | 3/1992 |
| WO | WO1993012227 A1 | 6/1993 |
| WO | WO1994025585 A1 | 11/1994 |
| WO | WO1994029351 A2 | 12/1994 |
| WO | WO1997013852 A1 | 4/1997 |
| WO | WO1998024884 A1 | 6/1998 |
| WO | WO1999045962 A1 | 9/1999 |
| WO | WO1999051642 A1 | 10/1999 |
| WO | WO1999058572 A1 | 11/1999 |
| WO | WO2000042072 A3 | 7/2000 |
| WO | WO2001014424 A2 | 3/2001 |
| WO | WO2011072204 A1 | 6/2001 |
| WO | WO2001058957 A3 | 8/2001 |
| WO | WO2002043478 A2 | 6/2002 |
| WO | WO2004016750 A2 | 2/2004 |
| WO | WO2004029207 A2 | 4/2004 |
| WO | WO2004035752 A2 | 4/2004 |
| WO | WO2004063351 A2 | 7/2004 |
| WO | WO2004074455 A2 | 9/2004 |
| WO | WO2004099249 A2 | 11/2004 |
| WO | WO2005040217 A2 | 5/2005 |
| WO | WO2005044853 A3 | 5/2005 |
| WO | WO2005070963 A1 | 8/2005 |
| WO | WO2005092925 A2 | 10/2005 |
| WO | WO2006020114 A2 | 2/2006 |
| WO | WO2009064854 A1 | 5/2009 |
| WO | WO2011097603 A1 | 8/2011 |
| WO | WO2011163311 A1 | 12/2011 |
| WO | WO2011163314 A1 | 12/2011 |
| WO | WO2012148873 A2 | 11/2012 |
| WO | WO2013044298 A1 | 4/2013 |
| WO | WO2014106602 A1 | 8/2014 |
| WO | WO2015073580 A1 | 2/2015 |

OTHER PUBLICATIONS

MacCallum et al., Antibody-antigen interactions: Contact analysis and binding site topography, J. Mol. Biol 262:732, 1996.*

Chen et al., Enhancement and destruction of antibody function by somatic mutation: unequal occurrence is controlled by V gene combinatorial association, EMBO J. 14(12):2784-2794, 1995.*

GenBank Database Accession No. AA104464.1, Tumor necrosis factor (ligand) superfamily, member 15 *Homo sapiens*] (Oct. 4, 2006), retrieved online Jun. 29, 2020.*

An et al., "IgG2m4, an engineered antibody isotype with reduced Fc function", (2009) MAbs 1:572-579.

Bruhns et al., "Specificity and affinity of human Fc receptors and their polymorphic variants for human IgG subclasses", Blood 2009, vol. 113:3716-3725.

Chen et al., "Influence of Histidine on the Stability and Physical Properties of a Fully Human Antibody in Aqueous and Solid Forms", (2003) Pharm Research vol. 20 No. 12:1952-1960.

Chu et al. "Inhibition of B cell receptor-mediated activation of primary human B cells by coengagement of CD19 and FcRIIb with Fc-engineered antibodies", (2008) Mol. Immunol. 45:3926-3933.

Davis et al., "Abatacept Binds to the Fc Receptor CD64 But Does Not Mediate Complement-Dependent Cytotoxicity or Antibody-Dependent Cellular Cytotoxicity", J Rheumatology 2007;34;2204-2210.

Dick et al. (2008) Biotechnology and Bioengineering, vol. 100, No. 6 pp. 1132-1143.

Dick et al., "Determination of the Origin of the N-Terminal Pyro-Glutamate Variation in Monoclonal Antibodies Using Model Peptides", (2007) Biotechnology and Bioengineering, vol. 97, No. 3, pp. 544-553.

(56) References Cited

OTHER PUBLICATIONS

Gala and Morrison, "V Region Carbohydrate and Antibody Expression", J Immunol 2004; 172:5489-5494.
Glaesner et al."Engineering and characterization of the long-actingglucagon-like peptide-1 analogue LY2189265, an Fcfusion protein", Diabetes Metab Res Rev 2010; 26: 287-296.
Gross et al., "TACI-lg Neutralizes Molecules Criticalfor B Cell Development and Autoimmune Disease:Impaired B Cell Maturation in Mice Lacking BLyS", (2001) Immunity 15:289-302.
Hambley and Gross, "Laser Flash Photolysis of Hydrogen Peroxideto Oxidize Protein Solvent-Accessible Residueson the Microsecond Timescale", J. American Soc. Mass Spectrometry, 2005, 16:2057-2063.
Horton et al., "Antibody-Mediated Coengagement of FcgRIIb and B Cell Receptor Complex Suppresses Humoral Immunity inSystemic Lupus Erythematosus", Journal of Immunology 2011; 186:4223-4233.
Hsu et al., "Enhanced adhesion of monocytes via reverse signaling triggered by decoy receptor 3", Exp. Cell Res., 292:241-51(2004).
Idusogie et al., "Mapping of the C1q Binding Site on Rituxan, a Chimeric Antibody with a Human IgG1 Fc", J Immunol 2000; 164:4178-4184.
Kim et al., "Identification of naturally secreted soluble form of TL1A,a TNF-like cytokine", Journal of Immunol. Methods, 298(1-2):1-8 (Mar. 2005).
Labrijn et al., "When binding is enough: nonactivating antibody formats", (2008) Curr. Op. Immunol. vol. 20:479-485.
Li et al., Optimization of humanized IgGs in glycoenginered Pichia pastoris, (2006) Nat. Biotechnol. vol. 24 No. 2, pp. 210-215.
Liu et al. "N-terminal Glutamate to Pyroglutamate Conversion in Vivofor Human IgG2 Antibodies", Journal of Biological Chemistry vol. 86, No. 13, pp. 11211-11217 , (2011).
Lonberg, "Human antibodies from transgenic animals", (2005) Nature Biotechnology, 23(9):1117-1125.
McEarchern et al., "Engineered anti-CD70 antibody with multiple effector functions exhibits in vitro and in vivo antitumor activities", (2007) Blood vol. 109:1185-1192.
Migone et al., "TL1A Is a TNF-like Ligand for DR3 and TR6/DcR3and Functions as a T Cell Costimulator", Immunity, 16:479-92 (2002).
Mimura et al., "The influence of glycosylation on the thermal stability and effector function expression of human IgG1-Fc: properties of a series of truncated glycoforms", (2000) Molecular Immunol 37:697-706.
Murray et al., "Epitope Affinity Chromatography and BiophysicalStudies of Monoclonal Antibodies and Recombinant Antibody Fragments", (2002) Journal of Chromatographic Science, vol. 40:343-349.
ATCC Product Sheet, Mus musculus, P3X63Ag8.653 ATCC® CRL1580, (2018).
Oganesyan et al., "Structural characterization of a human Fc fragment engineered for lack of effector functions", (2008) Acta Crystallogr. D. Biol. Crystallogr. D64:700-704.
Reddy et al., "Elimination of Fc Receptor-Dependent Effector Functions of a Modified IgG4 Monoclonal Antibody to Human CD4", (2000) J. Immunol. vol. 164:1925-1933.
Bother et al., "Discovery and development of the complementinhibitor eculizumab for the treatment ofparoxysmal nocturnal hemoglobinuria", (2007) Nat. Biotechnol. vol. 25:1256-1264.
Roversi et al., "Modelling prior distributions of atoms for macromolecular refinement and completion", Acta Cryst. Section D, 2000, D56:1313-1323.
Roy Jefferis & Marie-Paule Lefranc (2009) Human immunoglobulin allotypes, mAbs, 1:4, 332-338, DOI: 10.4161/mabs.1.4.9122.
Salfeld, "Isotype selection in antibody engineering", Nature Biotechnol. 25:1369-1372, (2007).
Sondermann et al., "The 3.2-A crystal structure of the humanIgG1 Fc fragment-FcgammaRlll complex", (2000) Nature, vol. 406:267-273.
Spiro, Protein glycosytation: nature, distribution, enzymatic formation, and disease implications of elveopeptide bonds, Glycobiolog vol. 12 No. 4 pp. 43R-56R, (2002).
Strohl, "Optimization of Fc-mediated effector functions of monoclonal antibodies", (2009) Current Opinion in Biotechnology, vol. 20:685-691.
Vafa et al., "An engineered Fc variant of an IgG eliminates all immune effector functions via structural perturbations", (2014) Methods, vol. 65:114-126.

* cited by examiner

TL1A.2-g4P Kappa Chain Nucleotide and Amino Acid Sequence

```
      A   I   Q   L   T   Q   S   P   S   S   L   S   A   S   V
  1   GCC ATC CAG TTG ACC CAG TCT CCA TCC TCC CTG TCT GCA TCT GTA

G   D   R   V   T   I   T   C   R   A   S   Q   G   I   S
 46   GGA GAC AGA GTC ACC ATC ACT TGC CGG GCA AGT CAG GGC ATT AGC

S   A   L   A   W   Y   Q   Q   K   P   G   K   A   P   K
 91   AGT GCT TTA GCC TGG TAT CAG CAG AAA CCA GGG AAA GCT CCT AAG

L   L   I   Y   D   A   S   S   L   E   S   G   V   P   S
136   CTC CTG ATC TAT GAT GCC TCC AGT TTG GAA AGT GGG GTC CCA TCA

R   F   S   G   S   G   S   G   T   D   F   T   L   T   I
181   AGG TTC AGC GGC AGT GGA TCT GGG ACA GAT TTC ACT CTC ACC ATC

S   S   L   Q   P   E   D   F   A   T   Y   Y   C   Q   Q
226   AGC AGC CTG CAG CCT GAA GAT TTT GCA ACT TAT TAC TGT CAA CAG

F   N   S   Y   P   L   T   F   G   G   G   T   K   V   E
271   TTT AAT AGT TAC CCT CTC ACT TTC GGC GGA GGG ACC AAG GTG GAG

I   K   R   T   V   A   A   P   S   V   F   I   F   P   P
316   ATC AAA CGT ACG GTG GCT GCA CCA TCT GTC TTC ATC TTC CCG CCA
```

FIG. 6

```
            S   D   E   Q   L   K   S   G   T   A   S   V   V   C   L
361         TCT GAT GAG CAG TTG AAA TCT GGA ACT GCC TCT GTT GTG TGC CTG

L   N   N   F   Y   P   R   E   A   K   V   Q   W   K   V
406         CTG AAT AAC TTC TAT CCC AGA GAG GCC AAA GTA CAG TGG AAG GTG

D   N   A   L   Q   S   G   N   S   Q   E   S   V   T   E
451         GAT AAC GCC CTC CAA TCG GGT AAC TCC CAG GAG AGT GTC ACA GAG

Q   D   S   K   D   S   T   Y   S   L   S   S   T   L   T
496         CAG GAC AGC AAG GAC AGC ACC TAC AGC CTC AGC AGC ACC CTG ACG

L   S   K   A   D   Y   E   K   H   K   V   Y   A   C   E
541         CTG AGC AAA GCA GAC TAC GAG AAA CAC AAA GTC TAC GCC TGC GAA

V   T   H   Q   G   L   S   S   P   V   T   K   S   F   N
586         GTC ACC CAT CAG GGC CTG AGC TCG CCC GTC ACA AAG AGC TTC AAC

R   G   E   C   *
631         AGG GGA GAG TGT TAG
```

FIG. 6
(CONTINUED)

TL1A.2-g4P Heavy Chain Nucleotide and Amino Acid Sequence

```
        Q   L   Q   L   Q   E   S   G   P   G   L   V   K   P   S
  1   CAG CTG CAG CTG CAG GAG TCG GGC CCA GGA CTG GTG AAG CCT TCG

E   T   L   S   L   T   C   T   V   S   G   G   S   I   S
 46   GAG ACC CTG TCC CTC ACC TGC ACT GTC TCT GGT GGC TCC ATC AGC

S   R   S   Y   Y   W   G   W   I   R   Q   P   P   G   K
 91   AGT AGG AGT TAC TAC TGG GGC TGG ATC CGC CAG CCC CCA GGG AAG

G   L   E   W   I   G   S   I   Y   Y   N   G   R   T   Y
136   GGA CTG GAG TGG ATT GGG AGT ATC TAT TAT AAT GGG AGA ACC TAC

Y   N   P   S   L   K   S   R   V   T   I   S   V   D   T
181   TAC AAC CCG TCC CTC AAG AGT CGA GTC ACC ATA TCC GTA GAC ACG

S   K   N   Q   F   S   L   K   L   S   S   V   T   A   A
226   TCC AAG AAC CAG TTC TCC CTG AAG CTG AGC TCT GTG ACC GCC GCA

D   T   A   V   Y   Y   C   A   R   E   D   Y   G   D   Y
271   GAC ACG GCT GTG TAT TAC TGT GCG AGG GAG GAC TAC GGT GAC TAC

G   A   F   D   I   W   G   Q   G   T   M   V   T   V   S
316   GGA GCT TTT GAT ATC TGG GGC CAA GGG ACA ATG GTC ACC GTC TCT

S   A   S   T   K   G   P   S   V   F   P   L   A   P   C
361   TCA GCT AGC ACC AAG GGC CCA TCC GTC TTC CCC CTG GCG CCC TGC
```

FIG. 7

```
        S   R   S   T   S   E   S   T   A   A   L   G   C   L   V
406     TCC AGG AGC ACC TCC GAG AGC ACA GCC GCC CTG GGC TGC CTG GTC

K   D   Y   F   P   E   P   V   T   V   S   W   N   S   G
451     AAG GAC TAC TTC CCC GAA CCG GTG ACG GTG TCG TGG AAC TCA GGC

A   L   T   S   G   V   H   T   F   P   A   V   L   Q   S
496     GCC CTG ACC AGC GGC GTG CAC ACC TTC CCG GCT GTC CTA CAG TCC

S   G   L   Y   S   L   S   S   V   V   T   V   P   S   S
541     TCA GGA CTC TAC TCC CTC AGC AGC GTG GTG ACC GTG CCC TCC AGC

S   L   G   T   K   T   Y   T   C   N   V   D   H   K   P
586     AGC TTG GGC ACG AAG ACC TAC ACC TGC AAC GTA GAT CAC AAG CCC

S   N   T   K   V   D   K   R   V   E   S   K   Y   G   P
631     AGC AAC ACC AAG GTG GAC AAG AGA GTT GAG TCC AAA TAT GGT CCC

P   C   P   P   C   P   A   P   E   F   L   G   G   P   S
676     CCA TGC CCA CCA TGC CCA GCA CCT GAG TTC CTG GGG GGA CCA TCA

V   F   L   F   P   P   K   P   K   D   T   L   M   I   S
721     GTC TTC CTG TTC CCC CCA AAA CCC AAG GAC ACT CTC ATG ATC TCC

R   T   P   E   V   T   C   V   V   V   D   V   S   Q   E
766     CGG ACC CCT GAG GTC ACG TGC GTG GTG GTG GAC GTG AGC CAG GAA
```

FIG. 7
(CONTINUED)

```
         D   P   E   V   Q   F   N   W   Y   V   D   G   V   E   V
 811    GAC CCC GAG GTC CAG TTC AAC TGG TAC GTG GAT GGC GTG GAG GTG

H   N   A   K   T   K   P   R   E   E   Q   F   N   S   T
 856    CAT AAT GCC AAG ACA AAG CCG CGG GAG GAG CAG TTC AAC AGC ACG

Y   R   V   V   S   V   L   T   V   L   H   Q   D   W   L
 901    TAC CGT GTG GTC AGC GTC CTC ACC GTC CTG CAC CAG GAC TGG CTG

N   G   K   E   Y   K   C   K   V   S   N   K   G   L   P
 946    AAC GGC AAG GAG TAC AAG TGC AAG GTC TCC AAC AAA GGC CTC CCG

S   S   I   E   K   T   I   S   K   A   K   G   Q   P   R
 991    TCC TCC ATC GAG AAA ACC ATC TCC AAA GCC AAA GGG CAG CCC CGA

E   P   Q   V   Y   T   L   P   P   S   Q   E   E   M   T
1036    GAG CCA CAG GTG TAC ACC CTG CCC CCA TCC CAG GAG GAG ATG ACC

K   N   Q   V   S   L   T   C   L   V   K   G   F   Y   P
1081    AAG AAC CAG GTC AGC CTG ACC TGC CTG GTC AAA GGC TTC TAC CCC

S   D   I   A   V   E   W   E   S   N   G   Q   P   E   N
1126    AGC GAC ATC GCC GTG GAG TGG GAG AGC AAT GGG CAG CCG GAG AAC

N   Y   K   T   T   P   P   V   L   D   S   D   G   S   F
1171    AAC TAC AAG ACC ACG CCT CCC GTG CTG GAC TCC GAC GGC TCC TTC
```

FIG. 7
(CONTINUED)

```
        F   L   Y   S   R   L   T   V   D   K   S   R   W   Q   E
1216   TTC CTC TAC AGC AGG CTA ACC GTG GAC AAG AGC AGG TGG CAG GAG

G   N   V   F   S   C   S   V   M   H   E   A   L   H   N
1261   GGG AAY GTC TTC TCA TGC TCC GTG ATG CAT GAG GCT CTG CAC AAC

H   Y   T   Q   K   S   L   S   L   S   L   G   K   *
1306   CAC TAC ACA CAG AAG AGC CTC TCC CTG TCT CTG GGT AAA TGA
```

```
      Q   L   Q   L   Q   E   S   G   P   G   L   V   K   P   S   E   T
1     CAG CTG CAG CTG CAG GAG TCG GGC CCA GGA CTG GTG AAG CCT TCG GAG ACC

___CDR1_____
      L   S   L   T   C   T   V   S   G   G   S   I   S   S   R   S   Y
52    CTG TCC CTC ACC TGC ACT GTC TCT GGT GGC TCC ATC AGC AGT AGG AGT TAC

Y   W   G   W   I   R   Q   P   P   G   K   G   L   E   W   I   G
103   TAC TGG GGC TGG ATC CGC CAG CCC CCA GGG AAG GGA CTG GAG TGG ATT GGG

_CDR2_____
      S   I   Y   Y   N   G   R   T   Y   Y   N   P   S   L   K   S   R
154   AGT ATC TAT TAT AAT GGG AGA ACC TAC TAC AAC CCG TCC CTC AAG AGT CGA

V   T   I   S   V   D   T   S   K   N   Q   F   S   L   K   L   S
205   GTC ACC ATA TCC GTA GAC ACG TCC AAG AAC CAG TTC TCC CTG AAG CTG AGS

_CDR3_____
      S   V   T   A   A   D   T   A   V   Y   Y   C   A   R   E   D   Y
256   TCT GTG ACC GCC GCA GAC ACG GCT GTG TAT TAC TGT GCG AGG GAG GAC TAC

G   D   Y   G   A   F   D   I   W   G   Q   G   T   M   V   T   V
307   GGT GAC TAC GGA GCT TTT GAT ATC TGG GGC CAA GGG ACA ATG GTC ACC GTC

S   S
358   TCT TCA
```

```
        A   I   Q   L   T   Q   S   P   S   S   L   S   A   S   V   G   D
  1    GCC ATC CAG TTG ACC CAG TCT CCA TCC TCC CTG TCT GCA TCT GTA GGA GAC

CDR1
        R   V   T   I   T   C   R   A   S   Q   G   I   S   S   A   L   A
 52    AGA GTC ACC ATC ACT TGC CGG GCA AGT CAG GGC ATT AGC AGT GCT TTA GCC

CDR2
        W   Y   Q   Q   K   P   G   K   A   P   K   L   L   I   Y   D   A
103    TGG TAT CAG CAG AAA CCA GGG AAA GCT CCT AAG CTC CTG ATC TAT GAT GCC

S   S   L   E   S   G   V   P   S   R   F   S   G   S   G   S   G
154    TCC AGT TTG GAA AGT GGG GTC CCA TAC AGG TTC AGC GGC AGT GGA TCT GGG

T   D   F   T   L   T   I   S   S   L   Q   P   E   D   F   A   T
205    ACA GAT TTC ACT CTC ACC ATC AGC AGC CTG CAG CCT GAA GAT TTT GCA ACT

CDR3
        Y   Y   C   Q   Q   F   N   S   Y   P   L   T   F   G   G   G   T
256    TAT TAC TGT CAA CAG TTT AAT AGT TAC CCT CTC ACT TTC GGC GGA GGG AAC

K   V   E   I   K
307    AAG GTG GAG ATC AAA
```

FIG. 9

```
  1          10          20          30          40
TSGSSHHHHH  HSSGIEGRGS  HMGDRMKQIE  DKIEEILSKI 50          60          70          80
YHIENEIARI  KKLIGERASQ  LRAQGEACVQ  FQALKGQEFA 90         100         110         120
PSHQQVYAPL  RADGDKPRAH  LTVVRQTPTQ  HFKNQFPALH 130         140         150         160
WEHELGLAFT  KNRMNYTNKF  LLIPESGDYF  IYSQVTFRGM 170         180         190         200
TSECSEIRQA  GRPNKPDSIT  VVITKVTDSY  PEPTQLLMGT 210         220         230         240
KSVCEVGSNW  FQPIYLGAMF  SLQEGDKLMV  NVSDISLVDY

250
TKEDKTFFGA  FLL
```

FIG. 10

TL1A ANTIBODIES AND USES THEREOF

FIELD OF THE INVENTION

The present invention is directed to antibodies against TL1A, and methods of making and using such antibodies. The antibodies are expected to be particularly useful in treating immunsystem diseases.

BACKGROUND OF THE INVENTION

Proteins that are structurally related to tumor necrosis factor (TNF) are collectively referred to as the TNF superfamily. TL1A, a TNF superfamily member, is a TNF-like cytokine that binds to the death-domain receptor (DR) 3 and provides costimulatory signals to activated lymphocytes. Through this interaction, TL1A induces secretion of IFN-gamma and may, therefore, participate in the development of T helper-1-type effector responses.

TL1A is a type II transmembrane protein and has been designated TNF superfamily member 15 (TNFSF15). TL1A is expressed predominantly by endothelial cells and monocytes, and its expression is inducible by TNF-a and IL-1a (Migone et al., Immunity, 16:479-92 (2002)). TL1A is upregulated by the proinflammatory cytokines TNF and IL-1 and also by immune complexes (IC) (Hsu et al., Exp. Cell Res., 292:241-51 (2004)).

TL1A mediates signaling via its cognate receptor DR3, a death receptor whose activation was known to induce both death and survival factors. TL1A, like TNF, is also presumed to circulate as a homotrimeric soluble form (Kim et al., J. Immunol. Methods, 298(1-2):1-8 (March 2005)).

TL1A binds with high affinity to death receptor 3 (DR3) which is a member of the death-domain containing TNF receptor family, and is also termed Wsl-1, Apo-3, TRAMP, and LARD, and now designated TNF receptor superfamily member 25 (TNFRSF25). Depending on the cell context, ligation of DR3 by TL1A can trigger one of two signaling pathways, activation of the transcription factor NF-kB or activation of caspases and apoptosis. TL1A functions in T cell costimulation and Th1 polarization. On activated T cells, TL1A functions specifically via its surface-bound receptor DR3 to promote cell survival and secretion of proinflammatory cytokines. The secreted decoy receptor 3 (DcR3), a soluble protein of the tumor necrosis factor receptor (TNFR) superfamily, blocks the action of TL1A (Kim et al., "Identification of naturally secreted soluble form of TL1A, a TNF-like cytokine," J Immunol Methods, 298: 1-8 (2005)).

Therefore, there remains a need in the art for compositions that can be used in the treatment of diverse inflammatory and immune diseases and disorders, such as allergy/asthma, rheumatoid arthritis, multiple sclerosis, Crohn's disease, inflammatory bowel disease, systemic lupus erythematosus (SLE), psoriasis, type 1 diabetes and transplant rejection. The present invention, directed to monoclonal antibodies against TL1A, satisfies this need.

SUMMARY OF THE INVENTION

The present invention is directed to isolated antibodies and antigen binding fragments thereof, that specifically bind to human TL1A and block binding to DR3, thereby inhibiting the immunostimulation signal that would otherwise occur in the TL1A-expressing cells.

The invention comprises an isolated antibody, or antigen binding fragment thereof, that competes for binding to human TL1A with antibody 10A4.

The invention comprises an isolated antibody, or antigen binding fragment thereof, that binds to TL1A at an epitope comprising one or more of residues 102-116(SEQ ID NO:16) or 166-180(SEQ ID NO: 17).

The invention comprises an isolated antibody or antigen binding fragment thereof that binds to TL1A at an epitope comprising one or more of residues of $^{169}$QAGR$^{172}$ (SEQ ID NO: 21) and one or more of residues of $^{113}$KNQF$^{116}$ (SEQ ID NO: 22). An embodiment of the invention comprises an isolated antibody or antigen binding fragment thereof that binds to TL1A at an epitope comprising the sequence $^{169}$QAGR$^{172}$ (SEQ ID NO: 21) or $^{113}$KNQF$^{116}$(SEQ ID NO: 22). An embodiment of the invention comprises an isolated antibody or antigen binding fragment thereof that binds to TL1A at an epitope comprising the sequence $^{169}$QAGR$^{172}$ (SEQ ID NO: 21) and $^{113}$KNQF$^{116}$(SEQ ID NO: 22).

The invention comprises an isolated anti-TL1A antibody or antigen binding fragment thereof that substantially inhibits the binding of human TL1A to DR3. An embodiment of the invention comprises an isolated antibody or antigen binding fragment thereof that binds to both human and cynomolgus TL1A.

The invention comprises an isolated antibody, or antigen binding fragment thereof, that binds to TL1A comprising a heavy chain variable domain comprising a CDRH1 sequence as shown in SEQ ID NO.:7; a CDRH2 sequence shown in SEQ ID NO.:8; and a CDRH3 sequence shown in SEQ ID NO.:9.

The invention comprises an isolated antibody, or antigen binding fragment thereof, that binds to TL1A comprising a light chain variable domain comprising a CDRL1 sequence shown in SEQ ID NO.:12; a CDRL2 sequence shown in SEQ ID NO.:13; and a CDRL3 sequence shown in SEQ ID NO.:14.

An embodiment of the invention comprises an isolated antibody, or antigen binding fragment thereof, that binds to TL1A comprising a heavy chain variable domain comprising a CDRH1 sequence as shown in SEQ ID NO.:7; a CDRH2 sequence shown in SEQ ID NO.:8; and a CDRH3 sequence shown in SEQ ID NO.:9 and a light chain variable domain comprising a CDRL1 sequence shown in SEQ ID NO.:12; a CDRL2 sequence shown in SEQ ID NO.:13; and a CDRL3 sequence shown in SEQ ID NO.:14.

The invention comprises an isolated antibody or antigen binding fragment comprising one or more heavy chains and one or more light chains, wherein the heavy chain comprises a heavy chain variable region having at least 80% sequence identity with the sequence of SEQ ID NO: 6; and the light chain comprises a light chain variable region having at least 80% sequence identity with the sequence of SEQ ID NO: 11.

The invention comprises a method of producing an anti-TL1A antibody or antigen binding fragment thereof comprising culturing a host cell transformed with an expression vector encoding the heavy and/or light chain variable region of the antibody or fragment under conditions that allows production of the antibody or fragment, and purifying the antibody from the cell.

An embodiment of the invention comprises a method of detecting the presence of TL1A in a sample comprising contacting the sample with the TL1A antibody, or antigen binding fragment of the invention under conditions that allow for formation of a complex between the antibody, or fragment and TL1A, and detecting the formation of the complex.

BRIEF DESCRIPTION OF THE DRAWINGS

FIG. 6 shows the TL1A.2-g4P kappa light chain nucleotide (SEQ ID NO: 1) and amino acid sequence (SEQ ID NO: 2)

FIG. 7 shows the heavy chain nucleotide (SEQ ID NO: 3) and amino acid sequence (SEQ ID NO: 4)

FIG. 8 shows the 10A4.F7 VH1 region nucleotide (SEQ ID NO: 5) and amino acid sequences (SEQ ID NO: 6). CDRH1, (SEQ ID NO: 7), CDRH2 (SEQ ID NO: 8) and CDRH3 (SEQ ID NO: 9) are indicated.

FIG. 9 shows the 10A4.F7 VL1 region nucleotide (SEQ ID NO: 10) and amino acid sequences (SEQ ID NO: 11). CDRL1, (SEQ ID NO: 12), CDRL2 (SEQ ID NO: 13) and CDRL3 (SEQ ID NO: 14) are indicated.

FIG. 10 (SEQ ID NO: 20) shows HDX-MS epitope mapping of 10A4. Epitope regions are underlined. Amino acid 85-101, (SEQ ID NO: 15), 102-116 (SEQ ID NO: 16) and 166-180 (SEQ ID NO: 17).

DETAILED DESCRIPTION OF THE PREFERRED EMBODIMENTS

Figure 1:
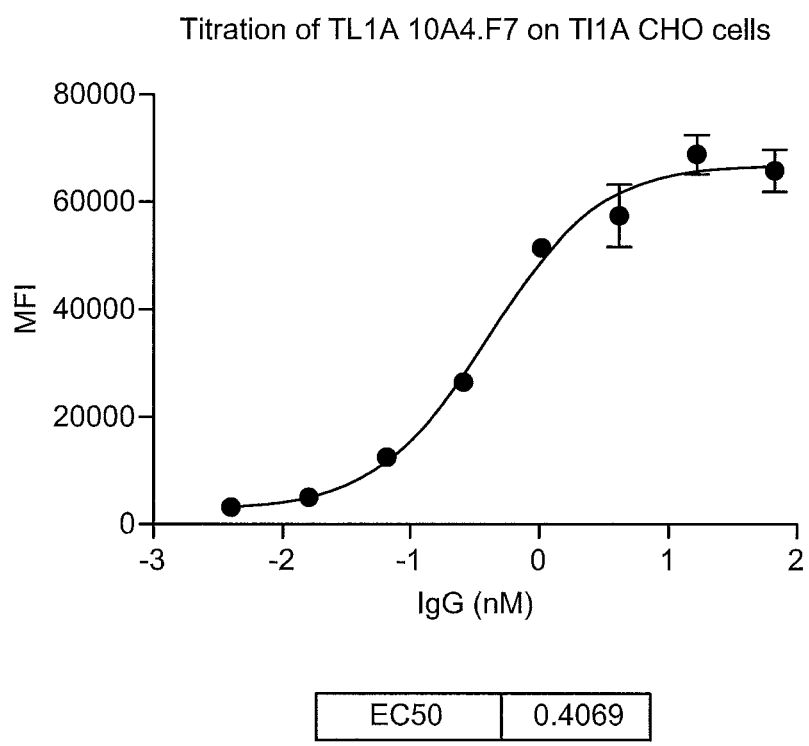
FIG. 1 shows the titration of monoclonal antibody 10A4.F7 on TL1A CHO cells. Dilutions of TL1A antibody were incubated with $10^5$ TL1A CHO cells in 100 ul FACS buffer for 1 hr. Cells were washed two times with FACS buffer and antibody binding was detected by staining with PE anti human Gig (Face specific) antibody and evaluated by FACS. The EC50 is 0.40 nM.

The present invention discloses isolated antibodies, particularly monoclonal antibodies, e.g. human monoclonal antibodies, that specifically bind to human TL1A and block binding to DR3, thereby inhibiting the immunostimulation signal that would otherwise occur in the TL1A-expressing cells. Provided herein are isolated antibodies, methods of making such antibodies and pharmaceutical compositions formulated to contain the antibodies or fragments. Also provided herein are methods of using the antibodies for immune suppression, alone or in combination with other immunosuppression agents. Accordingly, the anti-huTL1A antibodies described herein may be used in a treatment for a wide variety of therapeutic applications, including, for example, treating immunsystem diseases.

Definitions

The term "antibody" as used herein may include whole antibodies and any antigen binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-7}$ to $10^{-11}$ M or less. Any $K_D$ greater than about 10−6 M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$M or less, even more preferably $5\times10^{-9}$M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human TL1A might also cross-react with TL1A from certain non-human primate species (e.g., cynomolgus monkey), but might not cross-react with TL1A from other species, or with an antigen other than TL1A.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., human IgG1, exist in several allotypes, which differ from each other in at most a few amino acids. "Antibody" may include, by way of example, monoclonal and polyclonal antibodies; chimeric and humanized antibodies; human and nonhuman antibodies; wholly synthetic antibodies; and single chain antibodies.

The term "antigen-binding portion" or "antigen binding fragment" of an antibody, as used herein, refers to one or more fragments of an antibody that retain the ability to specifically bind to an antigen (e.g., human TL1A). Examples of binding fragments encompassed within the term "antigen-binding portion/fragment" of an antibody include (i) a Fab fragment—a monovalent fragment consisting of the $V_L$, $V_H$, CL and CH1 domains; (ii) a F(ab')$_2$ fragment—a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, and (v) a dAb fragment (Ward et al., (1989) Nature 341:544-546) consisting of a $V_H$ domain. An isolated complementarity determining region (CDR), or a combination of two or more isolated CDRs joined by a synthetic linker, may comprise and antigen binding domain of an antibody if able to bind antigen.

Unless otherwise indicated, the word "fragment" when used with reference to an antibody, such as in a claim, refers to an antigen binding fragment of the antibody, such that "antibody or fragment" has the same meaning as "antibody or antigen binding fragment thereof."

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

The phrases "an antibody recognizing an antigen" and "an antibody specific for an antigen" are used interchangeably herein with the term "an antibody which binds specifically to an antigen."

An "isolated antibody," as used herein, is intended to refer to an antibody that is substantially free of other antibodies having different antigenic specificities (e.g., an isolated antibody that specifically binds to TL1A is substantially free of antibodies that specifically bind antigens other than TL1A). An isolated antibody that specifically binds to an epitope of TL1A may, however, have cross-reactivity to other TL1A proteins from different species.

As used herein, an antibody that "inhibits binding of TL1A to DR3" refers to an antibody that inhibits the binding of human TL1A to human DR3 with an EC50 of about 1 µg/mL or less, such as about 0.9 µg/mL or less, about 0.85 µg/mL or less, about 0.8 µg/mL or less, about 0.75 µg/mL or less, about 0.7 µg/mL or less, about 0.65 µg/mL or less, about 0.6 µg/mL or less, about 0.55 µg/mL or less, about 0.5 µg/mL or less, about 0.45 µg/mL or less, about 0.4 µg/mL or less, about 0.35 µg/mL or less, about 0.3 µg/mL or less, about 0.25 µg/mL or less, about 0.2 µg/mL or less, about 0.15 µg/mL or less, or about 0.1 µg/mL or less, in art-recognized methods, e.g., in a FACS-based cell-binding assay.

The term "epitope" or "antigenic determinant" refers to a site on an antigen (e.g., TL1A) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation.

The term "epitope mapping" refers to the process of identification of the molecular determinants on the antigen involved in antibody-antigen recognition. Methods for determining what epitopes are bound by a given antibody are well known in the art and include, for example, immunoblotting and immunoprecipitation assays, wherein overlapping or contiguous peptides from (e.g., from TL1A) are tested for reactivity with a given antibody (e.g., anti-TL1A antibody); x-ray crystallography; 2-dimensional nuclear magnetic resonance; yeast display; and HDX-MS (see Example 8 herein); (see, e.g., *Epitope Mapping Protocols in Methods in Molecular Biology*, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on TL1A" with the antibodies described herein include, for example, epitope mapping methods, such as, x-ray analyses of crystals of antigen:antibody complexes, which provides atomic resolution of the epitope, and hydrogen/deuterium exchange mass spectrometry (HDX-MS) (see Example 8 herein). Other methods monitor the binding of the antibody to antigen fragments (e.g. proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) *Science* 244:1081) or yeast display of mutant target sequence variants. In addition, computational combinatorial methods for epitope mapping can also be used. These methods rely on the ability of the antibody of interest to affinity isolate specific short peptides from combinatorial phage display peptide libraries. Antibodies having the same or closely related VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb. Protoc.; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al. (1983) Methods in Enzymology 9:242); solid phase direct biotin-avidin EIA (see Kirkland et al. (1986) *J. Immunol.* 137:3614); solid phase direct labeled assay, solid phase direct labeled sandwich assay (see Harlow and Lane (1988), *Antibodies: A Laboratory Manual*, Cold Spring Harbor Press); solid phase direct label RIA using 1-125 label (see Morel et al. (1988) *Mol. Immunol.* 25(1):7); solid phase direct biotin-avidin EIA (Cheung et al. (1990) *Virology* 176:546); and direct labeled RIA. (Moldenhauer et al. (1990) *Scand. J. Immunol.* 32:77).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human TL1A, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human TL1A" refers to an antibody that binds to soluble or cell bound human TL1A with a $K_D$ of $10^{-7}$ M or less, such as approximately less than $10^{-8}$ M, $10^{-9}$M or $10^{-10}$ M or even lower. An antibody that "cross-reacts with cynomolgus TL1A" refers to an antibody that binds to cynomolgus TL1A with a $K_D$ of $10^{-7}$ M or less, such as approximately less than $10^{-8}$ M, $10^{-9}$ M or $10^{-10}$M or even lower.

The term "$k_{assoc}$" or "$k_a$", as used herein, refers to the association rate constant of a particular antibody-antigen interaction, whereas the term "$k_{dis}$" or "$k_d$," as used herein, refers to the dissociation rate constant of a particular antibody-antigen interaction. The term "$K_D$", as used herein, refers to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a BIACORE® surface plasmon resonance system or flow cytometry and Scatchard analysis.

The term "EC50" in the context of an in vitro or in vivo assay using an antibody or antigen binding fragment thereof, refers to the concentration of an antibody or an antigen-binding fragment thereof that induces a response that is 50% of the maximal response, i.e., halfway between the maximal response and the baseline.

The term "binds to immobilized TL1A" refers to the ability of an antibody described herein to bind to TL1A, for example, expressed on the surface of a cell or attached to a solid support.

The term "cross-reacts," as used herein, refers to the ability of an antibody described herein to bind to TL1A from a different species. For example, an antibody described herein that binds human TL1A may also bind TL1A from another species (e.g., cynomolgus TL1A). As used herein, cross-reactivity may be measured by detecting a specific reactivity with purified antigen in binding assays (e.g., SPR, ELISA) or binding to, or otherwise functionally interacting with, cells physiologically expressing TL1A. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses)

that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" to the antibody sequence provided herein, i.e. nucleotide and amino acid sequence modifications that do not abrogate the binding of the antibody encoded by the nucleotide sequence or containing the amino acid sequence, to the antigen. For example, modifications can be introduced by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-TL1A antibody is preferably replaced with another amino acid residue from the same side chain family. Methods of identifying nucleotide and amino acid conservative substitutions that do not eliminate antigen binding are well-known in the art. See, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

Alternatively, in another embodiment, mutations can be introduced randomly along all or part of an anti-TL1A antibody coding sequence, such as by saturation mutagenesis, and the resulting modified anti-TL1A antibodies can be screened for improved binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=# of identical positions/total # of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For coding sequences, these mutations may affect amino acid sequence as desired. In particular, DNA sequences substantially homologous to or derived from native V, D, J, constant, switches and other such sequences described herein are contemplated.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") in general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be TL1A or a fragment thereof, either as a soluble protein construct or as expressed on the surface of a cell.

An "immunomodulator" or "immunoregulator" refers to an agent, e.g., a component of a signaling pathway that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" (e.g., referring to inhibition/blocking of binding of TL1A to DR3) are used interchangeably and encompass both partial and complete inhibition/blocking. In some embodiments, the anti-TL1A antibody inhibits binding of DR3 to TL1A by at least about 50%, for example, at least about 60%, 70%, 80%, 90%, 95%, 99%, or 100%.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The terms "patient" and "subject" refer to any human or non-human animal that receives either prophylactic or therapeutic treatment. For example, the methods and compositions described herein can be used to treat immune system disease. The term "non-human animal" includes all vertebrates, e.g., mammals and non-mammals, such as non-human primates, sheep, dog, cow, chickens, amphibians, reptiles, etc.

As used herein, "immune system disease" include, but not limited to psoriasis, lupus (e.g. lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, Crohn's disease, inflammatory bowel disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases, polymyositis, scleroderma, and mixed connective tissue disease.

As used herein, "rheumatic diseases" means any disease that affects the joints, bone, soft tissue, or spinal cord (Mathies, H. 1983 Rheuma) and comprises inflammatory rheumatism, degenerative rheumatism, extra-articular rheumatism, and collagen diseases. Additionally, rheumatic diseases include, but are not limited to, chronic polyarthritis, psoriasis arthropathica, ankylosing spondylitis, rheumatoid arthritis, panarteriitis nodosa, systemic lupus erythematosus, progressive systemic scleroderma, periarthritis humeroscapularis, arthritis uratica, chondrocalcinosis, dermatomyositis, muscular rheumatism, myositis, and myogelosis. Some rheumatic diseases are known to be autoimmune diseases caused by a subject's altered immune response.

Various aspects described herein are described in further detail in the following subsections.

I. Anti-TL1A Antibodies

The present application discloses fully human anti-huTL1A antibodies having desirable properties for use as a therapeutic agent in treating immune system diseases. These properties include the ability to bind to human TL1A with high affinity, the ability to bind to cynomolgus monkey TL1A and the ability to block DR3 binding (and thus signaling).

The anti-TL1A antibody disclosed herein by sequence bind to specific epitopes on human TL1A determined as described in Example 8 and 9. Accordingly, other antibodies that bind to the same or closely related epitopes would likely share these desirable properties.

In addition, antibody 10A4.F7.2E8 binds to cynomolgus monkey TL1A, which is convenient when it is necessary to perform toxicity studies in support of regulatory approval for use of the antibody as a human therapeutic. Other anti-TL1A antibodies that bind to the same or similar epitopes as 10A4.F7.2E8 are likely to share this advantageous property of binding to cyno TL1A. Antibodies binding to similar epitopes can be discovered by doing competition experiments or by determining their epitopes directly.

Anti-TL1A Antibodies that Compete with Anti-huTL1A Antibodies Disclosed Herein

Anti-huTL1A antibodies that compete with the antibody of the present invention for binding to huTL1A, such as 10A4.F7.2E8, may be raised using immunization protocols similar to those described herein (Example 1). Antibodies that compete for binding with the anti-huTL1A antibodies described herein may also be generated by immunizing mice with human TL1A or a construct comprising the extracellular domain thereof (residues 72-251 of SEQ ID NO: 19), or by immunizing with a fragment of human TL1A containing the epitope bound by the anti-TL1A antibody disclosed herein (e.g. 10A4.F7.2E8). The resulting antibodies can be screened for the ability to block binding of 10A4.F7.2E8 to human TL1A by methods well known in the art, for example blocking binding to fusion protein of the extracellular domain of TL1A and an immunoglobulin Fc domain in a ELISA, or blocking the ability to bind to cells expressing huTL1A on their surface, e.g. by FACS. In various embodiments, the test antibody is contacted with the TL1A-Fc fusion protein (or to cells expressing huTL1A on their surface) prior to, at the same time as, or after the addition of 10A4.F7.2E8. Antibodies that reduce binding of 10A4.F7.2E8 to TL1A (either as an Fc fusion or on a cell), particularly at roughly stoichiometric concentrations, are likely to bind at the same, overlapping, or adjacent epitopes, and thus may share the desirable functional properties of 10A4.F7.2E8.

Competing antibodies can also be identified using other methods known in the art. For example, standard ELISA assays or competitive ELISA assays can be used in which a recombinant human TL1A protein construct is immobilized on the plate, various concentrations of unlabeled first antibody are added, the plate is washed, labeled second antibody is added, washed, and the amount of bound label is measured. If the increasing concentration of the unlabeled (first) antibody (also referred to as the "blocking antibody") inhibits the binding of the labeled (second) antibody, the first antibody is said to inhibit the binding of the second antibody to the target on the plate, or is said to compete with the binding of the second antibody. Additionally or alternatively, BIACORE® SPR analysis can be used to assess the ability of the antibodies to compete. The ability of a test antibody to inhibit the binding of an anti-huTL1A antibody described herein to TL1A demonstrates that the test antibody can compete with the antibody for binding to TL1A.

Accordingly, provided herein are anti-TL1A antibodies that inhibit the binding of an anti-huTL1A antibodies described herein to TL1A on cells by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% and/or whose binding to TL1A on cells is inhibited by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%, e.g., as measured by ELISA or FACS.

Typically, the same experiment is then conducted in the reverse, i.e., the first antibody is the second antibody and the second antibody is the first antibody. In certain embodiments, an antibody at least partially (e.g., at least 10%, 20%, 30%, 40%, 50%, 60%, 70%, 80%, or 90%) or completely (100%) blocks the binding of the other antibody to the target, e.g. human TL1A or fragment thereof, and regardless of whether inhibition occurs when one or the other antibody is the first antibody. A first and a second antibody "cross-block" binding of each other to the target, when the antibodies compete with each other both ways, i.e., in competition experiments in which the first antibody is added first and in competition experiments in which the second antibody is added first.

Anti-huTL1A antibodies are considered to compete with the anti-huTL1A antibodies disclosed herein if they inhibit binding of 10A4.F7.2E8 to human TL1A by at least 10%, 20%, 30%, 40%, 50%, 60%, 70%, 80%, 90% or by 100% when present at roughly equal concentrations.

Anti-TL1A Antibodies that Bind to the Same Epitope

Anti-huTL1A antibodies that bind to the same or similar epitopes to the antibodies disclosed herein may be raised using immunization protocols similar to those described herein (Example 1). The resulting antibodies can be screened for high affinity binding to human TL1A (Example 4). Selected antibodies can then be studied in Hydrogen/deuterium exchange mass spectrometry (HDX-MS) method (Example 8) to determine the precise epitope bound by the antibody. Antibodies that bind to the same or similar epitopes on human TL1A as antibody 10A4.F7.2E8 are likely to share the desirable functional properties of 10A4.F7.2E8.

Figure 11:
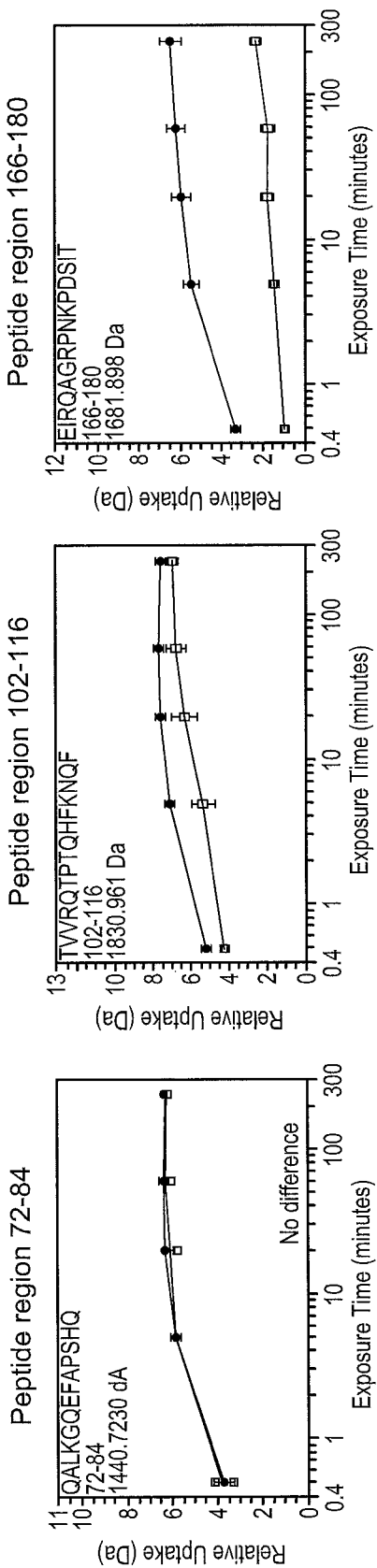
FIG. 11 shows a representative HDX kinetic curves of two peptide regions, amino acid 102-116 and 166-180 of TL1A, showed significant protections by 10A4 (curve marked by white squares vs. curve marked by black dots). Non epitope region 72-84 (SEQ ID NO: 18), on the other hand, showed no change in deuterium uptake upon mAb binding.

Epitope determinations may be made by any method known in the art. The epitopes disclosed herein were determined by HDX-MS and computational, as described at Example 8 and 9, and presented at FIGS. 10-12. In various embodiments, anti-huTL1A antibodies are considered to bind to the same epitope as an anti-huTL1A mAb disclosed herein, e.g. 10A4.F7.2E8, if they make contact with one or more of the same residues within at least one region of huTL1A contacted by 10A4.F7.2E8; if they make contacts with a majority of the residues within at least one region of huTL1A contacted by 10A4.F7.2E8; if they make contacts with a majority of the residues within each region of huTL1A contacted by 10A4.F7.2E8; if they make contact with a majority of contacts along the entire length of huTL1A contacted by 10A4.F7.2E8; if they make contacts within all of the distinct regions of human TL1A contacted by 10A4.F7.2E8; if they make contact with all of the residues at any one region on human TL1A contacted by 10A4.F7.2E8; or if they make contact with all residues at all regions contacted by contacted by 10A4.F7.2E8. Epitope "regions" are clusters of residues along the primary sequence that are contacted by antibodies 10A4.F7.2E8, e.g. as provided at SEQ ID NOs: 16 and 17.

HDX-MS measurements on 10A4 in TL1A indicate that 10A4 has a discontinuous epitope comprised of two peptide regions in TL1A with the region 1 having the most significant changes in deuterium uptake (FIG. 10 (SEQ ID NO: 20) & 11):

Peptide region 1 (166-180): EIRQAGRPNKPDSIT (SEQ ID NO: 17)

Peptide region 2 (102-116): TVVRQTPTQHFKNQF (SEQ ID NO:16)

The potential epitope regions were cross-verified by HDX-MS measurements on 10A4 Fab in TL1A. Utility of deuterated peptide fragmentation in MS further refined the spatial resolution of epitope to the following: epitope 1 $^{169}$QAGR$^{172}$ (SEQ ID NO: 21) and epitope 2 $^{113}$KNQF$^{116}$ (SEQ ID NO: 22).

Techniques for determining antibodies that bind to the "same epitope on TL1A" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. Methods may also rely on the ability of an antibody of interest to affinity isolate specific short peptides (either in native three dimensional form or in denatured form) from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes (see Example 9).

The epitope or region comprising the epitope can also be identified by screening for binding to a series of overlapping peptides spanning TL1A. Alternatively, the method of Jespers et al. (1994) *Biotechnology* 12: 899 may be used to guide the selection of antibodies having the same epitope and therefore similar properties to the an anti-TL1A antibodies described herein. Using phage display, first the heavy chain of the anti-TL1A antibody is paired with a repertoire of (preferably human) light chains to select a TL1A-binding antibody, and then the new light chain is paired with a repertoire of (preferably human) heavy chains to select a (preferably human) TL1A-binding antibody having the same epitope or epitope region as an anti-huTL1A antibody described herein. Alternatively variants of an antibody described herein can be obtained by mutagenesis of cDNA encoding the heavy and light chains of the antibody.

Alanine scanning mutagenesis, as described by Cunningham & Wells (1989) *Science* 244: 1081, or some other form of point mutagenesis of amino acid residues in TL1A may also be used to determine the functional epitope for an anti-TL1A antibody.

The epitope or epitope region (an "epitope region" is a region comprising the epitope or overlapping with the epitope) bound by a specific antibody may also be determined by assessing binding of the antibody to peptides comprising fragments of TL1A. A series of overlapping peptides encompassing the sequence of TL1A (e.g., human TL1A) may be synthesized and screened for binding, e.g. in a direct ELISA, a competitive ELISA (where the peptide is assessed for its ability to prevent binding of an antibody to TL1A bound to a well of a microtiter plate), or on a chip. Such peptide screening methods may not be capable of detecting some discontinuous functional epitopes, i.e. functional epitopes that involve amino acid residues that are not contiguous along the primary sequence of the TL1A polypeptide chain.

An epitope may also be identified by MS-based protein footprinting, such Fast Photochemical Oxidation of Proteins (FPOP). FPOP may be conducted as described, e.g., in Hambley & Gross (2005) *J. American Soc. Mass Spectrometry* 16:2057, the methods of which are specifically incorporated by reference herein.

The epitope bound by anti-TL1A antibodies may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in TL1A when free and when bound in a complex with an antibody of interest (Zinn-Justin et al. (1992) *Biochemistry* 31:11335; Zinn-Justin et al. (1993) *Biochemistry* 32:6884).

With regard to X-ray crystallography, crystallization may be accomplished using any of the known methods in the art (e.g. Giege et al. (1994) *Acta Crystallogr. D* 50:339; McPherson (1990) *Eur. J. Biochem.* 189:1), including microbatch (e.g. Chayen (1997) *Structure* 5:1269), hanging-drop vapor diffusion (e.g. McPherson (1976) *J. Biol. Chem.* 251:6300), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al., eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323), the disclosures of which are hereby incorporated by reference in their entireties.

Anti-TL1A Antibodies that Bind with High Affinity

In some embodiments the anti-huTL1A antibodies of the present invention bind to huTL1A with high affinity, like the anti-huTL1A antibodies disclosed herein, increasing their likelihood of being effective therapeutic agents. In various embodiments anti-huTL1A antibodies of the present invention bind to huTL1A with a $K_D$ of less than 10 nM, 5 nM, 2 nM, 1 nM, 300 pM or 100 pM. In other embodiments, the anti-huTL1A antibodies of the present invention bind to huTL1A with a $K_D$ between 2 nM and 100 pM. Standard assays to evaluate the binding ability of the antibodies toward huTL1A include ELISAs, Western blots, BIA-CORE® SPR analysis and RIAs.

Anti-TL1A Antibody Sequence Variants

Some variability in the antibody sequences disclosed herein may be tolerated and still maintain the desirable properties of the antibody. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Accordingly, the present invention further provides anti-huTL1A antibodies comprising CDR sequences that are at least 70%, 75%, 80%, 85%, 90%, 95%, 96%, 97%, 98%, or 99% identical to the CDR sequences of the antibodies disclosed herein (e.g. 10A4.F7.2E8). The present invention also provides anti-huTL1A antibodies comprising heavy and/or light chain variable domain sequences that are at least 70%, 75%, 80%, 85%, 90%, 95%, 96%, 97%, 98%, or 99% identical to the heavy and/or light chain variable domain sequences of the antibodies disclosed herein (e.g. 10A4.F7.2E8).

Anti-TL1A Antibodies Derived from the Same Germlines

Given that antigen-binding specificity is determined primarily by the CDRs, antibodies sharing CDRs sequences with antibodies disclosed herein (e.g. 10A4.F7.2E8) are likely to share their desirable properties.

In certain embodiments, anti-huTL1A antibodies of the present invention comprises a heavy chain variable region derived from a particular human germline heavy chain immunoglobulin gene and/or a light chain variable region from a particular human germline light chain immunoglobulin gene. Antibody 10A4 has a heavy chain derived from human germlines V4-39, D4-17 and JH3, and light chain germlines VK1 and JK4. Other antibodies that bind to human TL1A and derived from some or all of these germline sequences are likely to be very closely related in sequence, particularly those derived from the same V-region genes, and thus would be expected to share the same desirable properties.

As used herein, a human antibody comprises heavy or light chain variable regions that are "derived from" a particular germline sequence if the variable regions of the antibody are obtained from a system that uses human germline immunoglobulin genes, and the antibody sequence is sufficiently related to the germline that it is more likely derived from the given germline than from any other. Such systems include immunizing a transgenic mouse carrying human immunoglobulin genes with the antigen of interest or screening a human immunoglobulin gene library displayed on phage with the antigen of interest. The human germline immunoglobulin sequence(s) from which the sequence of an antibody is "derived" can be identified by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "derived from" a particular human germline immunoglobulin sequence may contain amino acid differences as compared to the germline sequence due to, for example, naturally-occurring somatic mutations or intentional introduction of site-directed mutation. However, a selected human antibody typically is at least 90% identical in amino acids sequence to an amino acid sequence encoded by a human germline immunoglobulin gene (e.g. V regions) and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene (e.g. V regions). Typically, a human antibody derived from a particular human germline sequence will display no more than 10 amino acid differences from the amino acid sequence encoded by the human germline immunoglobulin gene (e.g. V regions). In certain cases, the human antibody may display no more than 5, or even no more than 4, 3, 2, or 1 amino acid difference from the amino acid sequence encoded by the germline immunoglobulin gene (e.g. V regions).

II. Engineered and Modified Antibodies $V_H$ and $V_L$ Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Such grafting is of particular use in humanizing non-human anti-TL1A antibodies that compete for binding with the anti-huTL1A antibodies disclosed herein and/or bind to the same epitope as the anti-huTL1A antibodies disclosed herein. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific reference antibodies by constructing expression vectors that include CDR sequences from the specific reference antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest. Preferably conservative modifications are introduced. The mutations may be amino acid additions, deletions, or preferably substitutions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-TL1A antibodies that have one or more methionine residues in the heavy and/or light chain CDRs replaced with amino acid residues that do not undergo oxidative degradation.

Similarly, deamidation sites may be removed from anti-TL1A antibodies, particularly in the CDRs.

Potential glycosylation sites within the antigen binding domain are preferably eliminated to prevent glycosylation that may interfere with antigen binding. See, e.g., U.S. Pat. No. 5,714,350.

Fcs and Modified Fcs

In addition to the activity of a therapeutic antibody arising from binding of the antigen binding domain to the antigen (e.g. blocking of a cognate ligand or receptor protein in the case of antagonist antibodies, or induced signaling in the case of agonist antibodies), the Fc portion of the antibody interact with the immune system generally in complex ways to elicit any number of biological effects. Effector functions, such as the Fc region of an immunoglobulin is responsible for many important antibody functions, such as antigen-dependent cellular cytotoxicity (ADCC), complement dependent cytotoxicity (CDC), and antibody-dependent cell-mediated phagocytosis (ADCP), result in killing of target cells, albeit by different mechanisms. There are five major classes, or isotypes, of heavy chain constant region (IgA, IgG, IgD, IgE, IgM), each with characteristic effector functions. These isotypes can be further subdivided into subclasses, for example, IgG is separated into four subclasses known as IgG1, IgG2, IgG3, and IgG4. IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to the neonatal Fc receptor (FcRn).

Antibodies of the present invention may comprise the variable domains of the invention combined with constant domains comprising different Fc regions, selected based on the biological activities (if any) of the antibody for the intended use. Salfeld (2007) *Nat. Biotechnol.* 25:1369. Human IgGs, for example, can be classified into four subclasses, IgG1, IgG2, IgG3, and IgG4, and each these of these comprises an Fc region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to FcγRIIA$_{H131}$, and with lower affinity to FcγRIIA$_{R131}$FcγRIIIA$_{V158}$; IgG4 binds to FcγRI, FcγRIIA, FcγRIIB, FcγRIIC, and FcγRIIIA$_{V131}$; and the inhibitory receptor FcγRIIB has a lower affinity for IgG1, IgG2 and IgG3 than all other Fcγ receptors. Bruhns et al. (2009) *Blood* 113:3716. Studies have shown that FcγRI does not bind to IgG2, and FcγRIIIB does not bind to IgG2 or IgG4. Id. In general, with regard to ADCC activity, human IgG1≥IgG3>>IgG4≥IgG2. As a consequence, for example, an IgG1 constant domain, rather than an IgG2 or IgG4, might be chosen for use in a drug where ADCC is desired; IgG3 might be chosen if activation of FcγRIIIA-expressing NK cells, monocytes of macrophages; and IgG4 might be chosen if the antibody is to be used to desensitize allergy patients. IgG4 may also be selected if it is desired that the antibody lack all effector function.

Accordingly, anti-TL1A variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v). See, e.g., Jefferis et al. (2009) *mAbs* 1:1). Selection of allotype may be influenced by the potential immunogenicity concerns, e.g. to minimize the formation of anti-drug antibodies.

Variable regions described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. Each of these embodiments is described in further detail below. The numbering of residues in the Fc region is that of the EU index of Kabat. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g. if sequences differ between naturally occurring isotypes, or if multiple mutations may be substituted at the position, they are separated by slashes (e.g. "X/Y/Z").

For example, one may make modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein. Exemplary Fc sequence variants are disclosed herein, and are also provided at U.S. Pat. Nos. 5,624,821; 6,277,375; 6,737,056; 6,194,551; 7,317,091; 8,101,720; PCT Patent Publications WO 00/42072; WO 01/58957; WO 04/016750; WO 04/029207; WO 04/035752; WO 04/074455; WO 04/099249; WO 04/063351; WO 05/070963; WO 05/04021.7, WO 05/092925 and WO 06/020114.

Reducing Effector Function

ADCC activity may be reduced by modifying the Fc region. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Sarmay et al. (1992) *Molec. Immunol.* 29 (5): 633-9 with regard to ADCC sites in IgG1. In one embodiment, the G236R and L328R variant of human IgG1 effectively eliminates FcγR binding. Horton et al. (2011) *J. Immunol.* 186:4223 and Chu et al. (2008) *Mol. Immunol.* 45:3926. In other embodiments, the Fc having reduced binding to FcγRs comprised the amino acid substitutions L234A, L235E and G237A. Gross et al. (2001) *Immunity* 15:289.

CDC activity may also be reduced by modifying the Fc region. Mutations at IgG1 positions D270, K322, P329 and P331, specifically alanine mutations D270A, K322A, P329A and P331A, significantly reduce the ability of the corresponding antibody to bind C1q and activate complement. Idusogie et al. (2000) *J Immunol.* 164:4178; WO 99/51642. Modification of position 331 of IgG1 (e.g. P331S) has been shown to reduce complement binding. Tao et al. (1993) *J Exp. Med.* 178:661 and Canfield & Morrison (1991) *J. Exp. Med.* 173:1483. In another example, one or more amino acid residues within amino acid positions 231 to 239 are altered to thereby reduce the ability of the antibody to fix complement. WO 94/29351.

In some embodiments, the Fc with reduced complement fixation has the amino acid substitutions A330S and P331S. Gross et al. (2001) *Immunity* 15:289.

For uses where effector function is to be avoided altogether, e.g. when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g. N297A). Alternatively, a hybrid construct of human IgG2 (CH1 domain and hinge region) and human IgG4 (CH2 and CH3 domains) has been generated that is devoid of effector function, lacking the ability to bind the FcγRs (like IgG2) and unable to activate complement (like IgG4). Rother et al. (2007) *Nat. Biotechnol.* 25:1256. See also Mueller et al. (1997) *Mol. Immunol.* 34:441; Labrijn et al. (2008) *Curr. Op. Immunol.* 20:479 (discussing Fc modifications to reduce effector function generally).

In other embodiments, the Fc region is altered by replacing at least one amino acid residue with a different amino acid residue to reduce all effector function(s) of the antibody. For example, one or more amino acids selected from amino acid residues 234, 235, 236, 237, 297, 318, 320 and 322 can be replaced with a different amino acid residue such that the antibody has decreased affinity for an effector ligand but retains the antigen-binding ability of the parent antibody. The effector ligand to which affinity is altered can be, for example, an Fc receptor (residues 234, 235, 236, 237, 297) or the C1 component of complement (residues 297, 318, 320, 322). U.S. Pat. Nos. 5,624,821 and 5,648,260, both by Winter et al.

One early patent application proposed modifications in the IgG Fc region to decrease binding to FcγRI to decrease ADCC (234A; 235E; 236A; G237A) or block binding to complement component C1q to eliminate CDC (E318A or V/K320A and K322A/Q). WO 88/007089. See also Duncan & Winter (1988) *Nature* 332:563; Chappel et al. (1991) *Proc. Nat'l Acad. Sci.* (USA) 88:9036; and Sondermann et al. (2000) *Nature* 406:267 (discussing the effects of these mutations on FcγRIII binding).

Fc modifications reducing effector function also include substitutions, insertions, and deletions at positions 234, 235, 236, 237, 267, 269, 325, and 328, such as 234G, 235G, 236R, 237K, 267R, 269R, 325L, and 328R. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V. These and other modifications are reviewed in Strohl (2009) *Current Opinion in Biotechnology* 20:685-691. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G2364, A327G, A330S and P331S in IgG1; E233P, F234V, L235A, optionally G2364 in IgG4; and A330S and P331S in IgG2. See Armour et al. (1999) *Eur. J. Immunol.* 29:2613; WO 99/58572. Other mutations that reduce effector function include L234A and L235A in IgG1 (Alegre et al. (1994) *Transplantation* 57:1537); V234A and G237A in IgG2 (Cole et al. (1997) *J. Immunol.* 159:3613; see also U.S. Pat. No. 5,834,597); and S228P and L235E for IgG4 (Reddy et al. (2000) *J. Immunol.* 164:1925). Another combination of mutations for reducing effector function in a human IgG1 include L234F, L235E and P331S. Oganesyan et al. (2008) *Acta Crystallogr. D. Biol. Crystallogr.* 64:700. See generally Labrijn et gal. (2008) *Curr. Op. Immunol.* 20:479. Additional mutations found to decrease effector function in the context of an Fc (IgG1) fusion protein (abatacept) are C226S, C229S and P238S (EU residue numbering). Davis et al. (2007) *J. Immunol.* 34:2204.

Other Fc variants having reduced ADCC and/or CDC are disclosed at Glaesner et al. (2010) *Diabetes Metab. Res. Rev.* 26:287 (F234A and L235A to decrease ADCC and ADCP in an IgG4); Hutchins et al. (1995) *Proc. Nat'l Acad. Sci. (USA)* 92:11980 (F234A, G237A and E318A in an IgG4); An et al. (2009) *MAbs* 1:572 and U.S. Pat. App. Pub. 2007/0148167 (H268Q, V309L, A330S and P331S in an IgG2); McEarchern et al. (2007) *Blood* 109:1185 (C226S, C229S, E233P, L234V, L235A in an IgG1); Vafa et al. (2014) *Methods* 65:114 (V234V, G237A, P238S, H268A, V309L, A330S, P331S in an IgG2).

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S. Gross et al. (2001) *Immunity* 15:289. These five substitutions may be combined with N297A to eliminate glycosylation as well.

III. Antibody Physical Properties

Antibodies described herein can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J. Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. In some instances, it is preferred to have an anti-TL1A antibody that does not contain variable region glycosylation. This can be achieved either by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG4 antibody typically falls within the pH range of 6-8. There is speculation that antibodies with a pI outside the normal range may have some unfolding and instability under in vivo conditions. Thus, it is preferred to have an anti-TL1A antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the $T_{MI}$ (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett.* 68:47-52) or circular dichroism (Murray et al. (2002) *J. Chromatogr. Sci.* 40:343-9)(see FIG. 5).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem.* 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

The anti-TL1A mAb 10A4, formatted as a human-IgG4 isotype (10A4-IgG4), was characterized by several standard biophysical techniques, and shown to have biophysical properties typical for a pure, monomeric and stable monoclonal antibody. For example, size-exclusion high performance liquid chromatography (SE-HPLC) coupled to a multi-angle laser light scattering detector (MALS) showed that samples of the antibody were more than 90% pure, with a main species having a MALS-determined mass of ~140 kDa. Dynamic light scattering determined a hydrodynamic radius of 5.3 nm, also consistent with what is expected for a monomeric antibody in solution. Differential scanning calorimetry data also showed that 10A4-IgG4 has high thermal stability, with 3 distinct thermal transitions having transition midpoint ($T_m$) values of 70.75° C., 84.698° C. and 88.50° C.

IV. Nucleic Acid Molecules Another aspect described herein pertains to nucleic acid molecules that encode the antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

V. Antibody Generation

Various antibodies of the present invention, e.g. those that compete with or bind to the same epitope as the anti-human TL1A antibodies disclosed herein, can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In one embodiment, the antibodies described herein are human monoclonal antibodies. Such human monoclonal antibodies directed against TL1A can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or x, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-TL1A antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-TL1A antibodies described herein. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-TL1A antibodies described herein.

Additional mouse systems described in the art for raising human antibodies, e.g., human anti-TL1A antibodies, include (i) the VELOCIMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to TL1A, transgenic or transchromosomal mice containing human immunoglobulin genes (e.g., HCo12, HCo7 or KM mice) can be immunized with a purified or enriched preparation of the TL1A antigen and/or cells expressing TL1A, as described for other antigens, for example, by Lonberg et al. (1994) *Nature* 368(6474): 856-859; Fishwild et al. (1996) *Nature Biotechnology* 14: 845-851 and WO 98/24884. Alternatively, mice can be immunized with DNA encoding human TL1A. Preferably, the mice will be 6-16 weeks of age upon the first infusion. For example, a purified or enriched preparation (5-50 µg) of the recombinant TL1A antigen can be used to immunize the HuMAb mice intraperitoneally. In the event that immunizations using a purified or enriched preparation of the TL1A antigen do not result in antibodies, mice can also be immunized with cells expressing TL1A, e.g., a cell line, to promote immune responses. Exemplary cell lines include TL1A-overexpressing stable CHO and Raji cell lines.

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-TL1A human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to TL1A

To generate hybridomas producing human monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

VI. Antibody Manufacture

Generation of Transfectomas Producing Monoclonal Antibodies to TL1A

Antibodies of the present invention, including both specific antibodies for which sequences are provided and other, related anti-TL1A antibodies, can be produced in a host cell transfectoma using, for example, a combination of recombinant DNA techniques and gene transfection methods as is well known in the art (Morrison, S. (1985) Science 229: 1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13). Antibodies of the present invention can also be produced in glycoengineered strains of the yeast Pichia pastoris. Li et al. (2006) Nat. Biotechnol. 24:210.

Preferred mammalian host cells for expressing the recombinant antibodies described herein include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bioeng.* 97:544; Liu et al. (2011) *JBC* 28611211; Liu et al. (2011) *Biol. Chem.* 286:11211.

VII. Assays

Antibodies described herein can be tested for binding to TL1A by, for example, standard ELISA. Briefly, microtiter plates are coated with purified TL1A at 1-2 µg/ml in PBS, and then blocked with 5% bovine serum albumin in PBS. Dilutions of antibody (e.g., dilutions of plasma from TL1A-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human TL1A, but not to a control cell line that does not express TL1A. Briefly, the binding of anti-TL1A antibodies is assessed by incubating TL1A expressing CHO cells with the anti-TL1A antibody at 1:20 dilution. The cells are washed and binding is detected with a PE-labeled anti-human IgG Ab. Flow cytometric analyses are performed using a FACScan flow cytometry (Becton Dickinson, San Jose, Calif.). Preferably, mice which develop the highest titers will be used for fusions.

An ELISA assay as described above can be used to screen for antibodies and, thus, hybridomas that produce antibodies that show positive reactivity with the TL1A immunogen. Hybridomas that produce antibodies that bind, preferably with high affinity, to TL1A can then be subcloned and further characterized. One clone from each hybridoma, which retains the reactivity of the parent cells (by ELISA), can then be chosen for making a cell bank, and for antibody purification.

To purify anti-TL1A antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-TL1A monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using TL1A coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing TL1A, flow cytometry can be used, as described in the Example 17. Briefly, cell lines expressing membrane-bound TL1A (grown under standard growth conditions) are mixed with various concentrations of monoclonal antibodies in PBS containing 0.1% BSA at 4° C. for 1 hour. After washing, the cells are reacted with Phycoerythrin (PE)-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-TL1A antibodies can be further tested for reactivity with the TL1A antigen by Western blotting. Briefly, cell extracts from cells expressing TL1A can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-TL1A antibodies include standard assays known in the art, for example, BIACORE® surface plasmon resonance (SPR) analysis using a BIACORE® 2000 SPR instrument (Biacore AB, Uppsala, Sweden).

In one embodiment, an antibody specifically binds to the extracellular region of human TL1A. An antibody may specifically bind to a particular domain (e.g., a functional domain) within the extracellular domain of TL1A. In a particular embodiment, the antibody specifically binds to the site on TL1A to which DR3 binds. In certain embodiments, the antibody specifically binds to the extracellular region of human TL1A and the extracellular region of cynomolgus TL1A. Preferably, an antibody binds to human TL with high affinity.

VIII. Compositions

Further provided are compositions, e.g., a pharmaceutical compositions, containing one or a combination of anti-TL1A antibodies, or antigen-binding fragment(s) thereof, described herein, formulated together with a pharmaceutically acceptable carrier.

In certain embodiments, a composition comprises an anti-TL1A antibody at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

Pharmaceutical compositions described herein also can be administered in combination therapy, i.e., combined with other agents. For example, the combination therapy can include an anti-TL1A antibody described herein combined with at least one other immunsuppresion agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 1 to 100 mg/kg, and more usually 1 to 50 mg/kg, of the host body weight. For example dosages can be 40 mg/kg body weight, 30 mg/kg body weight, 20 mg/kg body weight, 15 mg/kg body weight, 10 mg/kg body weight or 5 mg/kg body weight or within the range of 1 to 20 mg/kg. An exemplary treatment regime entails administration once per week, once every two weeks, once every three weeks, once every four weeks, once a month, once every 3 months or once every three to 6 months An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is maintenance or therapeutic. In maintenance applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a maintenance regime.

Actual dosage levels of the active ingredients in the pharmaceutical compositions described herein may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-TL1A antibody described herein preferably results in a decrease in severity of disease symptoms, an increase in frequency and duration of disease symptom-free periods, or a prevention of impairment or disability due to the disease affliction.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-TL1A antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

IX. Uses and Methods

The antibodies, antibody compositions and methods described herein have numerous in vitro and in vivo utilities involving, for example, suppression of immune response by blocking TL1A signaling, or detection of TL1A. In a preferred embodiment, the antibodies described herein are human antibodies. For example, anti-TL1A antibodies described herein can be administered to cells in culture, in vitro or ex vivo, or to human subjects, e.g., in vivo, to supress immunity in a variety of diseases. Accordingly, provided herein are methods of modifying an immune response in a subject comprising administering to the subject an antibody, or antigen-binding fragment thereof, described herein such that the immune response in the subject is modified. Preferably, the response is inhibited, suppressed or down-regulated.

Also encompassed are methods for detecting the presence of human TL1A antigen in a sample, or measuring the amount of human TL1A antigen, comprising contacting the sample, and a control sample, with a human monoclonal antibody, or an antigen binding fragment thereof, which specifically binds to human TL1A, under conditions that allow for formation of a complex between the antibody or fragment thereof and human TL1A. The formation of a complex is then detected, wherein a difference complex formation between the sample compared to the control sample is indicative the presence of human TL1A antigen in the sample. Moreover, the anti-TL1A antibodies described herein can be used to purify human TL1A via immunoaffinity purification.

EXAMPLES

Example 1

TL1A Immunization and Fusion

KM Immunizations:

To generate fully human monoclonal antibodies to TL1A, a KM Mouse™ was immunized (Table 1) with purified recombinant TL1A antigen (R&D Systems 1319-TL/CF).

TABLE 1

TL1A Fusion 2596

| Mouse Strain | Mouse | Fusion | Titer at Fusion | Lymphocytes Fused | TL1A Positive Hybridomas |
|---|---|---|---|---|---|
| KM | 238401 | 2596 | 4050 | $5 \times 10^7$ | 70 |

15 ug of soluble TL1A plus 5 ug of TNP labeled TL1A in Ribi adjuvant was Injected SC plus hock on days 0, 5, 8, 11, 15, and 18 followed by fusion on day 22.

A mixture on 15 ug of native antigen, and 5 ug of TNP modified antigen in Ribi adjuvant was injected in the Hock plus multiple sites subcutaneous (SC) on days 0, 5, 8, 11, 15 and 18 followed by fusions of spleen and lymph node B cells on day 22. TNP modified TL1A was made by mixing 5 ul of picryl sulfonic acid (Sigma 92822) with 1 mg of TL1A for 4 hr at 4 C followed by overnight dialysis with PBS.

Generation of Hybridomas Producing Human Monoclonal Antibodies to BTLA:

The lymphocytes isolated from the KM Mice™, were fused to a mouse myeloma cell line by electrofusion. Electrofusion is accomplished by using an electric current to align lymphocytes and myeloma cells between electrodes in a Cytopluse™ fusion cuvett, and then briefly increasing the electric potential across the cell membranes. The brief pulse of electric current destabilizes membranes opening a pore between adjacent cells. During this process the membranes of adjacent cells fuse leading to a hybrid myeloma: lymphocyte (hydbridoma) cell.

Single cell suspensions of lymphocytes from immunized mice were fused to an equal number of the P3X63-Ag8.653 nonsecreting mouse myeloma cells (ATCC, CRL 1580) by electrofusion. Cells were plated at approximately $2.5 \times 10^4$ in flat bottom microtiter plates, followed by incubation in selective medium containing 10% FBS, 3-5% Origen (IGEN), OPI supplement (Sigma 0 5003: $1.1 \times 10^{-3}$ M Oxalo acetic acid, $4.5 \times 10^{-4}$ M sodium Pyruvate, 4 mM L-glutamine, 0.055 mM 2-mercaptoethanol, and 1×HAT (Sigma H0262). After approximately one week, cells were cultured in medium in which the HAT is replaced with HT (Sigma H0137). Individual wells were then screened by an automated homogenous assay to select wells producing human IgG Kappa antibodies. Subsequently, these human IgG positive wells were screened by ELISA on TL1A antigen coated plates to select hybridomas secreting TL1A specific human IgG Kappa antibodies. The antibody-secreting hybridomas were replated to 24 well plates, screened again and, if they were still producing antibody specific for TL1A, cells were preserved be freezing at −80 c or in liquid nitrogen (LN2). Anti-TL1A monoclonal antibodies were subcloned at least twice by limiting dilution. The stable subclones were then cultured in vitro to generate small amounts of antibody in tissue culture medium for further characterization. Frozen aliquots of subclones were preserved by freezing in LN2.

The naming protocol used for this hybridoma: TL1A 2596.10A4.F7.2E8 is as follows. The antibody is specific for TL1A and was derived from fusion 2596. The parental clone was isolated from plate 10 well A4. 10A4.F7 is a subclone of parental clone 10A4, and 10A4.F7.2E8 is a subclone of 10A4.F7.

Characterization of Antibody Binding to Antigen

Antibodies of the disclosure can be tested for binding to TL1A by, for example, standard ELISA. Briefly, microtiter plates are coated with purified TL1A at 1.0 μg/ml in PBS, and then blocked with 1% bovine serum albumin in PBS/tween. Dilutions of antibody (e.g., dilutions of plasma from TL1A-immunized mice, or cell culture supernatants) are added to each well and incubated for 1-2 hours at ambient temperature. The plates are washed with PBS/Tween and then incubated with secondary reagent (e.g., for human antibodies, a goat-anti-human IgG Fc-specific polyclonal reagent) conjugated to horseradish peroxidase for 1 hour at ambient temperature. After washing, the plates are developed with ABTS (2,2'-Azino-bis-(3-ethylbenzthiazoline-6-sulfonic acid) substrate (Moss Substrates, 1.46 mmol/L), and analyzed at OD of 405.

An ELISA assay as described above can also be used to screen for hybridomas that show positive reactivity with TL1A immunogen. Hybridomas that bind with high avidity to TL1A are subcloned and further characterized. One clone from each hybridoma, which retains the reactivity of the parent cells (by ELISA), can be chosen for making a 5-10 vial cell bank stored at −140° C., and for antibody purification.

To purify anti-TL1A antibodies, selected hybridomas can be grown to a volume of 1-2 L in tissue culture flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-TL1A monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using TL1A coated-ELISA plates as described above. Biotinylated mAb binding can be detected with a streptavidin-peroxidase probe. Additionally, similar competition studies can be done by FACS on TL1A-CHO cells. Binding of TL1A antibodies to cells can be detected with an anti human Ig-phycoerythrin probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific horseradish peroxidase-conjugated probes. Plates are developed and analyzed as described above.

FACS assays were used to verify that antibodies of the disclosure are binding to native TL1A expressed on cells. Briefly, dilutions of antibody in PBS 1% BSA plus 0.5% sodium azide (FACS buffer) were incubated with transfected CHO cells expressing TL1A ($10^5$ cells) for 30-60 minutes at 4 C. Cells were washed twice by centrifugation, aspiration of supernatant, and addition of fresh FACS buffer. Antibody binding to TL1A on cells was detected by incubating the cells in PE (Phycoerythrin) labeled goat anti-human IgG (Fc specific) antibody for 30 min at 4 C, washing the cells 2× as above, and analyzing by FACS (FIG. 1).

Figure 2:
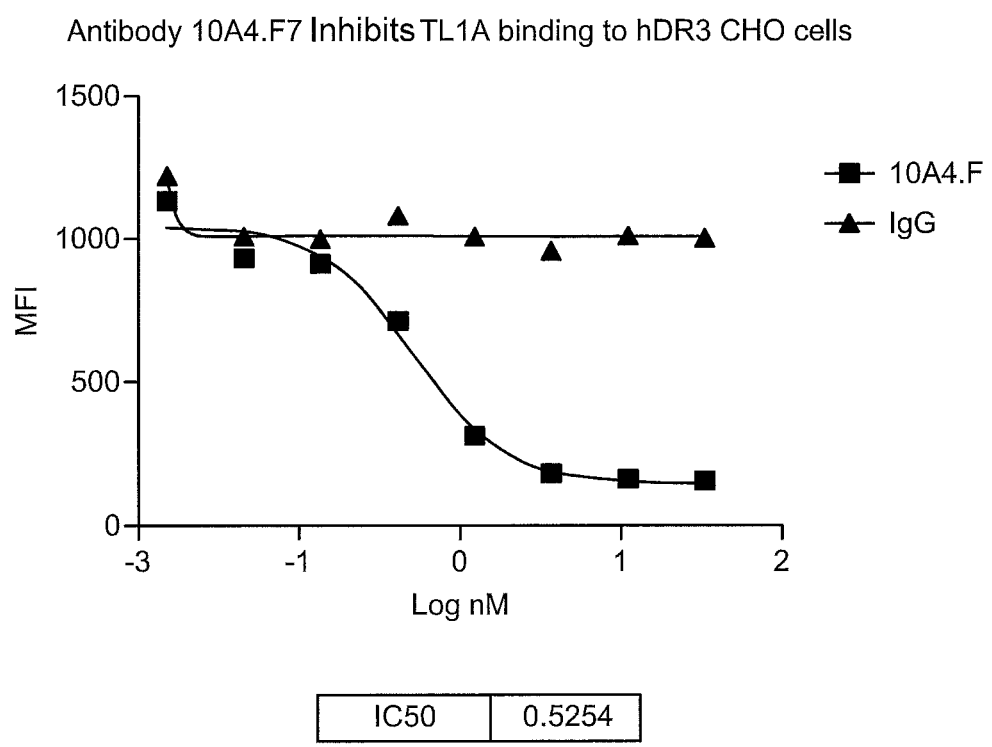
FIG. 2 shows inhibition of TL1A binding to hDR3 CHO cells by antibody 10A4.F7. TL1A SH6 at 200 ng/ml (50 ul) was incubated with dilutions of 10A4.F7 (50 ul) antibody or control IgG1 antibody (all reagents in FACS buffer). The mixture was incubated for 30 minutes and then added to $10^5$ hDR3 CHO cells in 100 ul of FACS buffer and incubated for 1 hr. Cells were washed twice in FACS buffer and TL1A binding to DR3 CHO cells was detected by staining cells with PE anti 6×His antibody (R&D systems) and evaluated by FACS. The IC50 in this experiment was 0.524 nM.

Identification of anti-TL1A antibodies that block TL1A binding to DR3 were also done by FACS by using soluble TL1A-SH6 protein (his tagged) binding to hDR3 expressed on CHO cells (DR3 CHO). Anti-TL1A or control antibodies were incubated with TL1A SH6 antigen at 0.1-0.5 ug/ml for 30 minutes in FACS buffer and then hDR3 CHO cells were added to the antibody TL1A mix and incubated for 30 minutes. Cells were washed and TL1A binding to hDR3 CHO cells was detected with PE anti-His antibody followed by FACS. Blocking antibodies prevent TL1A SH6 from binding to hDR3 CHO cells (FIG. 2).

Example 2

Anti-TL1A Antibody Purification

The original Anti-TL1A antibody from hybridoma, 1490-2596-10A4.F7.2E8 was expressed as a recombinant protein in CHO cells and was termed TL1A.2. This protein was expressed as G4P Fc version as well as G1.1 f Fc version. Supernatants obtained from CHO cells were purified on a MabSelectSure Protein A column. Briefly, CHO supernatant was loaded on to a Protein A column that was pre-equilibrated with PBS (phosphate buffered saline), pH 7.4. The column was washed extensively with PBS after the sample loading followed by elution of the bound protein using 0.1 M citrate buffer, pH 3.0. The eluted protein was brought to neutral pH immediately by the addition appropriate amount of 1 M Tris buffer. The sample was then buffer exchanged to PBS by extensive dialysis.

The concentration of the purified antibody was determined by measuring the absorbance of the protein at 280 nm. An absorbance of 1.4 at 280 nm was considered to be equal to 1 mg/mL of antibody. Purity of the antibody was confirmed by Bioanalyzer as well as CE-SDS methods. Endotoxin levels in the purified samples were measured by LAL kinetic method.

The aggregation levels were determined by SEC-HPLC as well as SEC-MALLS methods. The identity of the antibody was confirmed by determining the N-terminal amino acid sequences of light and heavy chains of antibody by Edman sequencing. The mass of light and heavy chains of the antibody was determined by LC-MS methods. The heterogeneity of the antibody was evaluated by hydrophobic interaction chromatography using TSK Ether 5PW column. The oligosaccharide profile of the antibody was determined by removing the glycan structures from the antibody using PNGAse F enzyme, fluorescent labeling of the oligos and further analysis by Capillary Electrophoresis method.

Example 3

Vector Construction and Expression

The 10A4 VK was amplified by PCR utilizing $V_K$ clone MP.1_06132012-A06 as the template, and cloned into vector pICOFSCneoK which contains the osteonectin signal sequence and the human kappa constant region, generating plasmid pICOFSCneoK (TL1A.10A4).

The 10A4 VH was amplified by PCR utilizing the $V_H$ clone MP.1_06132012-E02 as the template, and cloned into vector pICOFSCpurG4P which contains the osteonectin signal sequence and the human IgG4-S228P constant region, generating plasmid pICOFSCpurG4P(TL1A.10A4). Plasmids pICOFSCpurG4P(TL1A.10A4) and pICOFSCneoK (TL1A.10A4) were co-transfected into CHO-S cells and a stable pool was selected and scaled up for the expression of TL1A.2-g4P for research use.

Example 4

Protocol for Affinity Measurement

Figure 3:
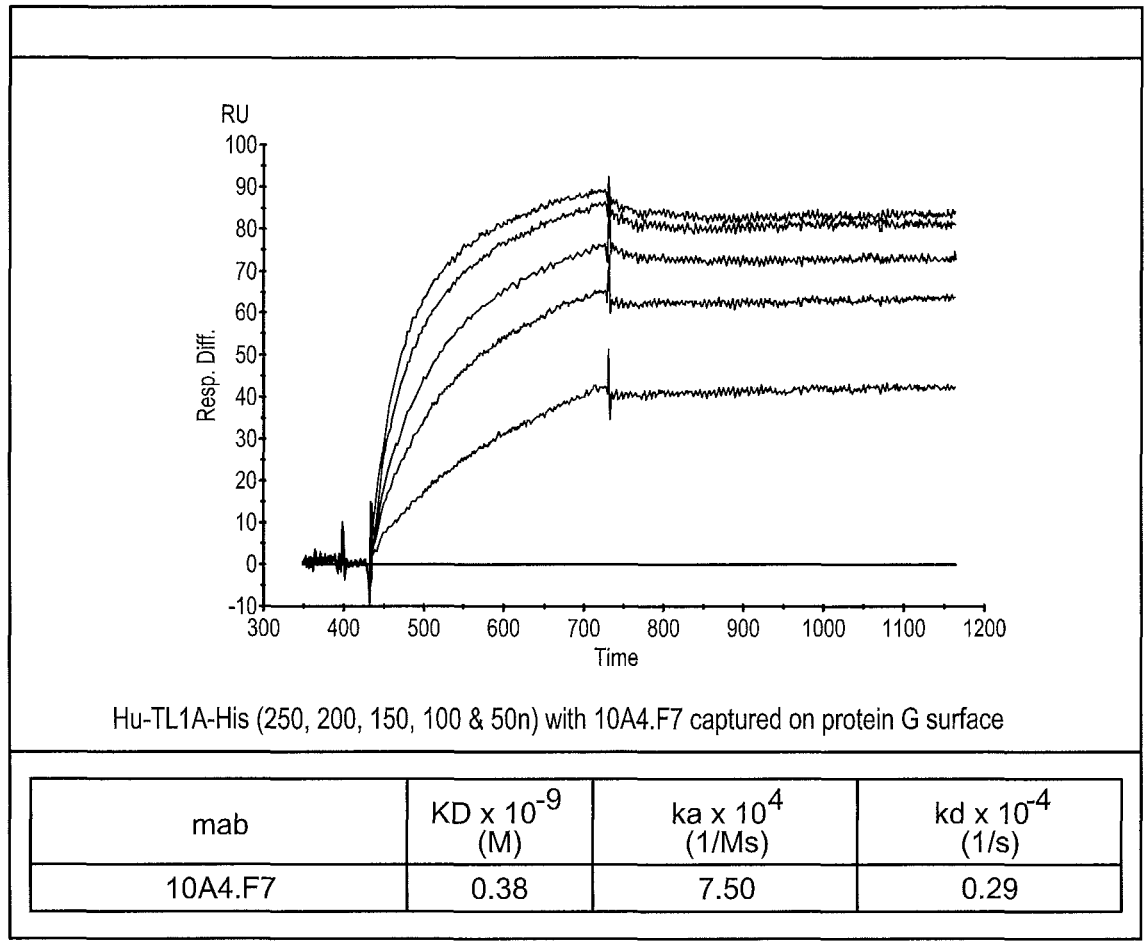
FIG. 3 shows a sensogram. Hu-TL1A-His (250, 200, 150, 100 & 50n) with 10A4.F7 captured on protein G surface

Protein G chip (CM5) was made by coating it ~400 Rus using acetate buffer (pH2.9). 10A4.F7 mab (7.5 ug/mL, 12 uL) was captured at 10 ug/L/min flow rate on Protein G surface. Hu-TL1A-His antigen (Lot#50182AS151) at multiple concentrations (250, 200, 150, 100 & 50 nM) were flowed over captured mab for 5 min at 25 ul/min and allowed to dissociate for 7.5 min. Protein G surface was regenerated with 10 uL of 50 mM NaOH and 5 uL of 25 mM HCL at 100 uL/min flow rate. Data was analyzed by using Biaevaluation 3.17 (FIG. 3).

Example 5

Protocol for Epitope Binding

Figure 4:
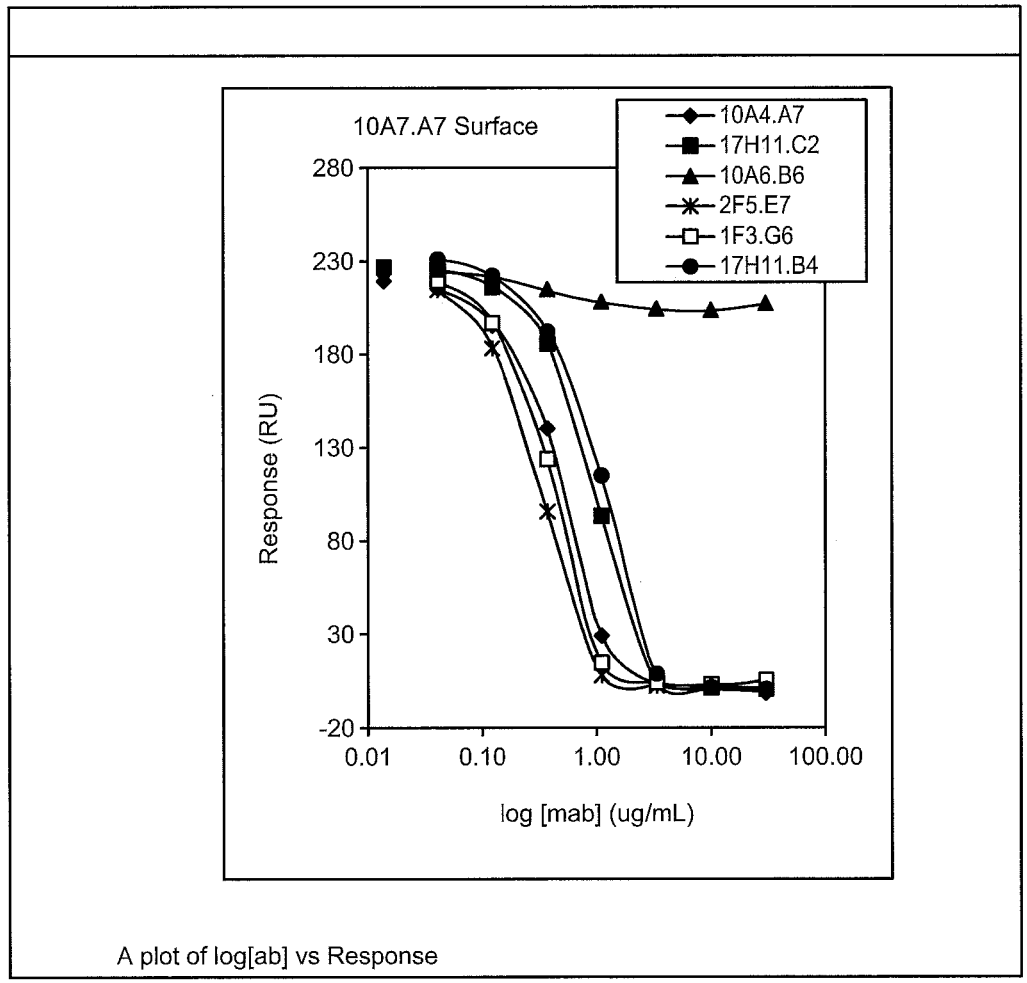
FIG. 4 shows a binding diagram.

10A4.A7 (4.6 KRUs), 17H11.C2 (6.3 KRUs) and 10A6.B6 (9.6 KRUs) were coated on the CM5 chip. Mabs were titrated down (1:3) starting 30 ug/mL & incubated with 25n Hu-TL1A-His antigen for ~2 hrs. Antibody-antigen complex injected on the mab coated surface for 2.5 minutes. Surface was regenerated with 25 mM NaOH. A plot was generated using log [Ab] vs. response where a decrease in antibody-antigen complex signal shows same epitope bin. (FIG. 4)

Example 6

Physical Stability of 10A4.7 by DSC

Figure 5:
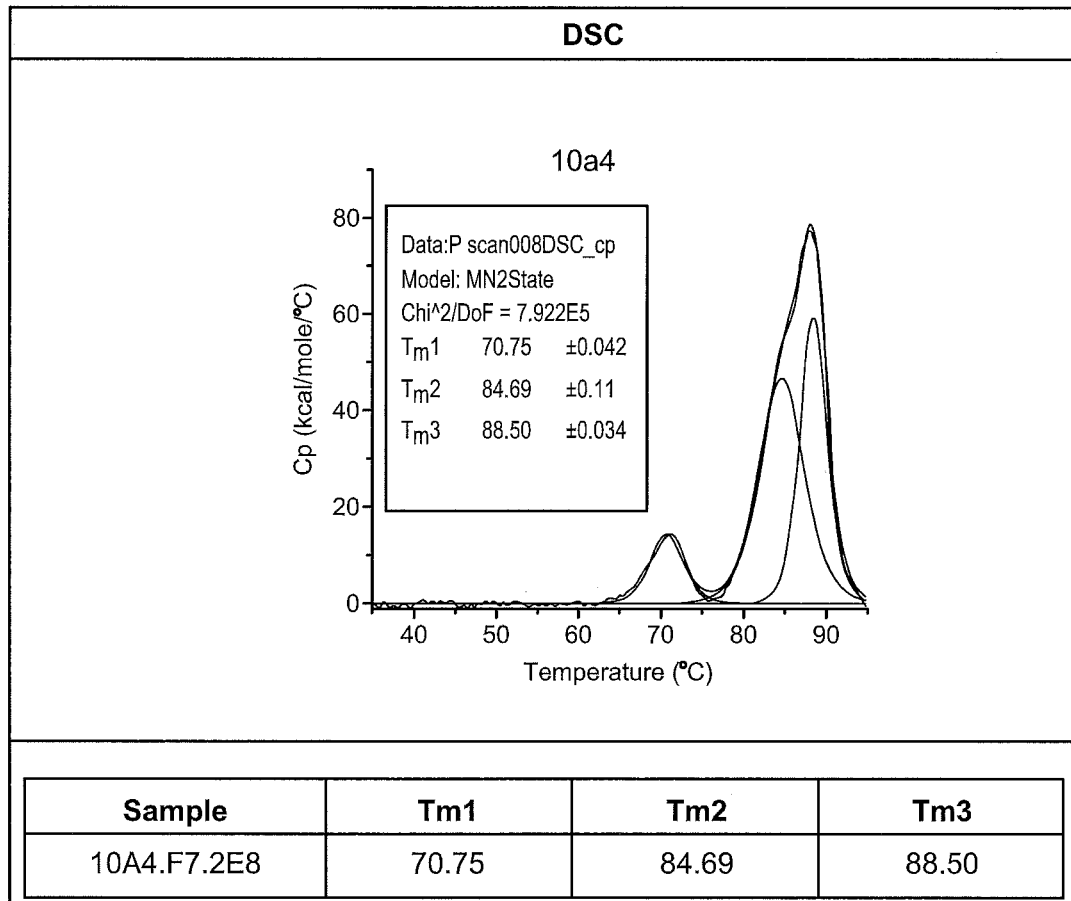
FIG. 5 shows the physical stability of 10A4.F7 by DSC

Physical stability of 10A4.7 was done by DSC FIG. 5.

Example 7

Variable Region Sequencing

Total RNA was prepared from hybridoma clone 1490.2596.10A4.F7.2E8 and $V_H$ and $V_K$ cDNAs were prepared in duplicate. Variable regions of the antibody were amplified by the rapid amplification of cDNA ends (RACE) procedure using a 3' human-specific constant region primer paired with the 5' RACE universal primer mix. The resultant PCR products containing the variable regions were cloned into the pCR4-TOPO vector. Templiphi samples were prepared from the TOPO clones and subjected to DNA sequencing. The resultant DNA sequences were analyzed for in-frame rearrangements and other antibody characteristics. The $V_H$ sequence from clone MP.1_06132012-E02(FIGS. 7 and 8) and the $V_K$ sequence from clone MP.1_06132012-A06 (FIGS. 6 and 9) were chosen as the representative sequences.

Example 8

TL1A/10A4 Epitope Mapping by HDX-MS

Hydrogen/deuterium exchange mass spectrometry (HDX-MS) method probes protein conformation and conformational dynamics in solution by monitoring the rate and extent of deuterium exchange of backbone amide hydrogen atoms. The level of HDX depends on the solvent accessibility of backbone amide hydrogen atoms and the protein hydrogen bonds. The mass increase of the protein upon HDX can be precisely measured by MS. When this technique is paired with enzymatic digestion, structure features at the peptide level can be resolved, enabling differentiation of surface exposed peptides from those folded inside. Typically, the deuterium labeling and subsequent quenching experiments are performed, followed by online pepsin digestion, peptide separation, and MS analysis.

Epitope mapping was performed on TL1A trimer with anti-TL1A mAb (10A4) and TL1A trimer with 10A4 Fab. Prior to epitope mapping experiments, non-deuterated experiments were carried out to generate a list of common peptic peptides for recombinant full length human TL1A trimer (4 µM) and protein complex of TL1A trimer with 10A4 or TL1A trimer with 10A4 Fab (1:3 molar ratio), achieving 80% sequence coverage for TL1A. In the HDX-MS experiment, 5 µL of each sample (TL1A or TL1A with mAb/Fab) was diluted into 55 µL of $D_2O$ buffer (10 mM phosphate buffer, $D_2O$, pD 7.0) to start the labeling reactions. The reactions were carried out for different periods of time: 30 sec, 5 min, 20 min, 60 min and 240 min. By the end of each labeling reaction period, the reaction was quenched by adding quenching buffer (100 mM phosphate buffer with 4M GdnCl, pH 2.5, 1:1, v/v) and 50 µL of quenched sample was injected into Waters HDX-MS system for analysis. The deuterium uptake levels of common peptic peptides were monitored in the absence/presence of 10A4 or 10A4 Fab (FIG. 10 (SEQ ID NO: 20)).

Example 9

TL1A/10A4 Epitope Mapping by Computational Modeling

Using the structure of TL1A trimer a computational analysis was performed. TNF-like ligand 1A (TL1A), binds its cognate receptor DR3 and the decoy receptor DcR3. TL1A belongs to the conventional TNF ligand family, which currently includes eight other members: FasL, LIGHT, TNFα, LTα, LTβ, TRAIL, RANKL and CD40L.

Human TL1A consists of 251 amino acids: 35 in the cytoplasmic domain, 24 in the transmembrane region, and 192 in the extracellular domain. There are two potential N-linked glycosylation sites in the TL1A amino acid sequence, Asn residues at positions 133 and 229. The TL1A structure shows a jelly-roll fold typical of the TNF superfamily. Members of the TNF superfamily are type-II transmembrane proteins that form noncovalent homotrimers which adopt the jelly-roll fold typical of the TNF family, with inner and outer β sheets composed of the A' AHCF and B' BGDE strands, respectively. The tightly packed trimer is typical of the TNF superfamily. The solvent accessible surface area of each monomer buried in the trimeric assembly is 1977 Å 2, comparable to that observed in other stable trimeric TNF ligands (TNFα, 2412 Å2; TRAIL, 2261 Å2; CD40L, 2091 Å2). Similar to other conventional TNF ligands, the subunit interface of TL1A is formed by interactions between the edges of the β-sandwich in one monomer (E and F strands) and the inner sheet of the neighboring monomer (A, H, C and F strands). The central region of this interface is composed predominantly of hydrophobic residues with F81, Y146, F182 and L184 from each monomer positioned to contribute to the hydrophobic core of the trimer. The corresponding residues at these four positions in other conventional TNF ligands are generally conserved and form the most prevalent interdomain hydrophobic contacts.

Figure 12:
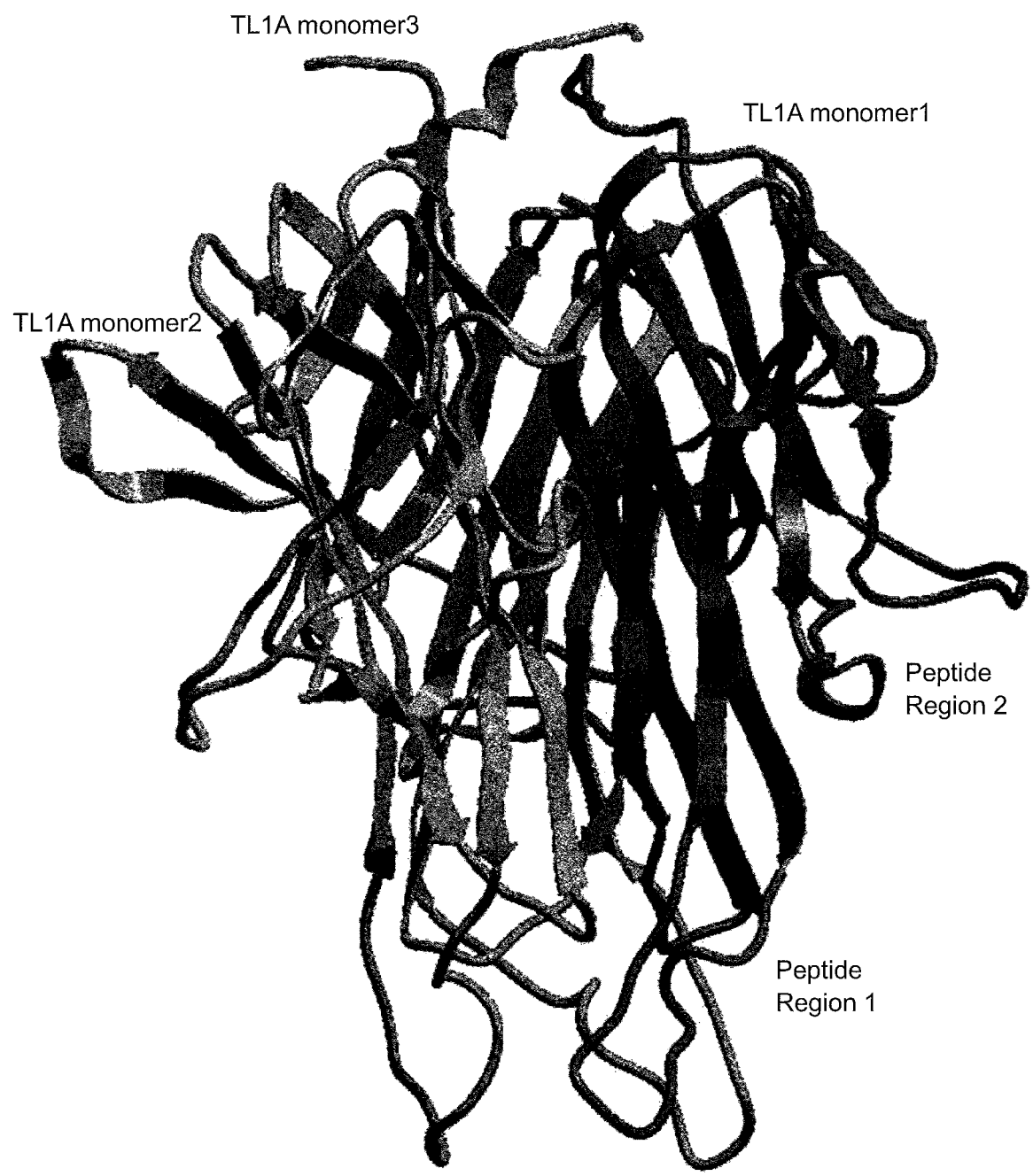
FIG. 12 shows the two regions of TL1A that were identified by HDX mapped onto the TL1A structure.
Figure 13:
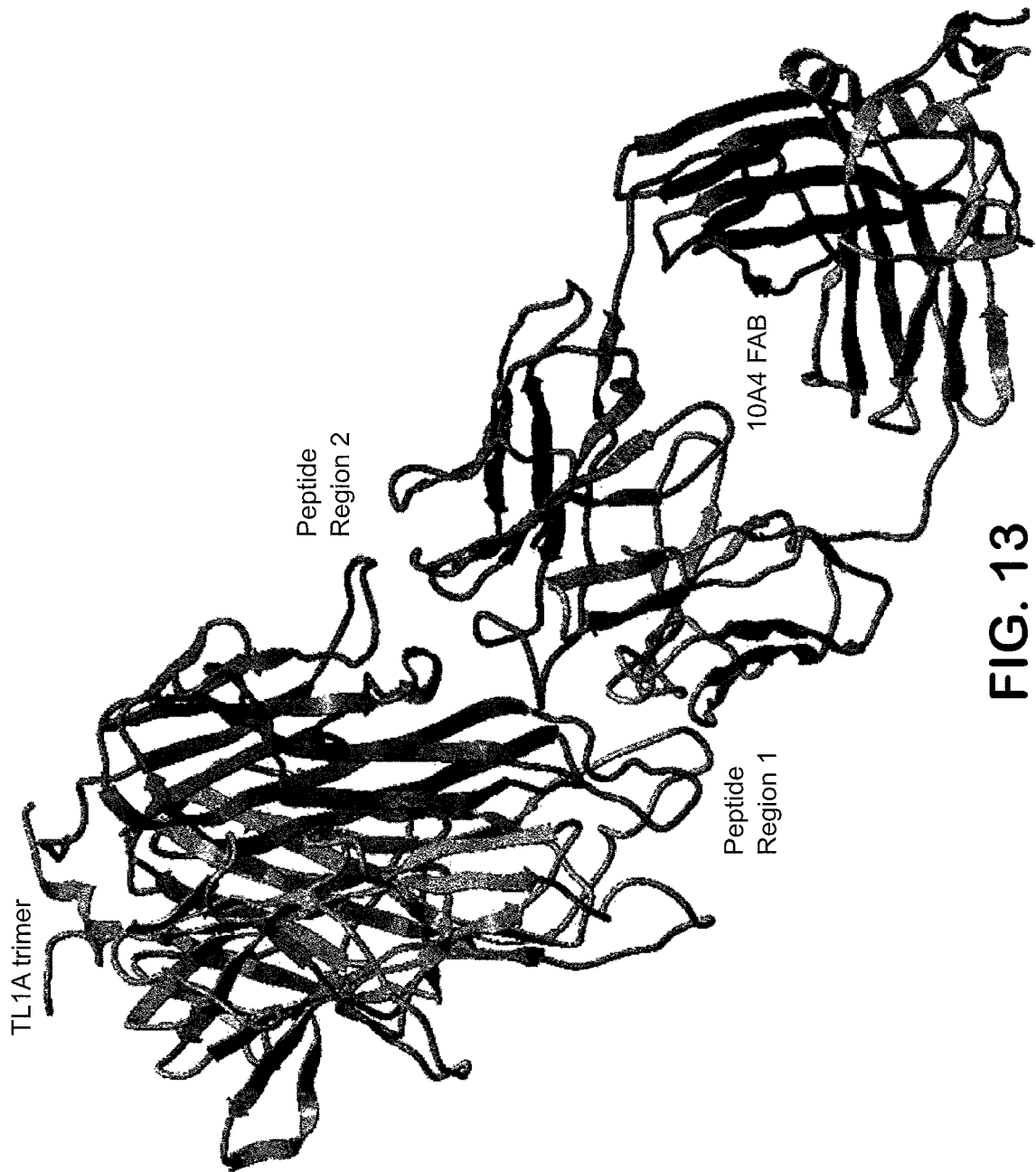
FIG. 13 shows the TL1A trimer with a FAB model for the 10A4 mAb showing that the discontinuous epitope in TL1A would require interactions from both the heavy and light chains. Peptide region 1 and Peptide region 2 form the discontinuous epitope exposed to solvent.

The two regions of TL1A that were identified by HDX were mapped onto the TL1A structure, FIG. 12. Peptide region 1 and Peptide region 2 form the discontinuous epitope exposed to solvent. FIG. 13 shows the TL1A trimer with a FAB model for the 10A4 mAb showing that the discontinuous epitope in TL1A would require interactions from both the heavy and light chains. Computational assessment of protein complexes show that selected residues located at protein interfaces can contribute significantly to protein-protein interaction energies. Residues that have been shown to contribute significantly to protein interactions include the aromatic amino acids (Tyr, Phe, Trp), basic amino acids (Arg, Lys), acidic amino acids (Asp, Glu) and polar amino acids (Gln, Asn, Ser, Thr).

Table 2 and 3 contain the computational assessment of exposed amino acids corresponding to Peptide Region 1 and 2. The tables show side chain exposure and percent side chain exposure which can be used to assess the accessibility for functional residues in these peptide regions. For Peptide region 1, Table 2, it is interesting to note that $E^{166}$, $R^{168}$, $Q^{169}$, $R^{172}$, and $K^{175}$ have function amino acid sides chains that are extremely exposed, 50-97%. Interestingly, there is good correlation with the data from peptide fragmentation MS spatial epitope for region 1 $^{169}QAGR^{172}$ (SEQ ID NO: 21) with the most exposed residue $Q^{169}$ at 97%. Both $R^{168}$ and $R^{172}$ are proxial to $Q^{169}$ in the TL1A structure demonstrating the correlation of modeling, three dimensional structure and HDX experiments.

TABLE 2

Computational assessment of exposed amino acids
corresponding to Peptide Region 1
SECSEIRQAGRPNKPDSIT (SEQ ID NO: 23)
EIRQAGRPNKPDSIT (SEQ ID NO: 24) (166-180)
93-107 - HDX Peptide Region 1

| Molecule | Residue | Side Chain Exposure | Percent Side chain Exposure | Critical Functional Amino Acid |
| --- | --- | --- | --- | --- |
| TL1A_A | E166 | 138.046707 | 0.738218 | X * |
| TL1A_A | I167 | 80.786659 | 0.416426 | |
| TL1A_A | R168 | 168.333267 | 0.68989 | X * |
| TL1A_A | Q169 | 184.482407 | 0.97096 | X * |
| TL1A_A | A170 | 81.956467 | 0.660939 | |
| TL1A_A | G171 | 78.1968 | 0.878616 | |
| TL1A_A | R172 | 126.085464 | 0.516744 | X * |
| TL1A_A | P173 | 91.752304 | 0.611682 | |
| TL1A_A | N174 | 30.269852 | 0.188012 | |
| TL1A_A | K175 | 168.50209 | 0.787393 | X * |

TABLE 2-continued

Computational assessment of exposed amino acids
corresponding to Peptide Region 1
SECSEIRQAGRPNKPDSIT (SEQ ID NO: 23)
EIRQAGRPNKPDSIT (SEQ ID NO: 24) (166-180)
93-107 - HDX Peptide Region 1

| Molecule | Residue | Side Chain Exposure | Percent Side chain Exposure | Critical Functional Amino Acid |
|---|---|---|---|---|
| TL1A_A | P176 | 66.328865 | 0.442192 | |
| TL1A_A | D177 | 67.25705 | 0.436734 | |
| TL1A_A | S178 | 67.517006 | 0.535849 | |
| TL1A_A | I179 | 1.554886 | 0.008015 | |
| TL1A_A | T180 | 11.607443 | 0.076365 | |

For Peptide Region 2 the most exposed functional residues are $H^{111}$, $F^{112}$, $K^{113}$, and $N^{114}$. These functional amino acids are also very exposed, 62-93% and form the second bulk of the discontinuous epitope. The functional residues identified by modeling correlate with the MS spatial epitope for region 2 identified by fragmentation MS $^{113}KNQF^{116}$ (SEQ ID NO: 22).

TABLE 3

Computational assessment of exposed amino acids
corresponding to Peptide Region 2
TPTQHFKNQFPALH (SEQ ID NO: 25)
TPTQHFKNQFPALH (SEQ ID NO: 25) (107-120) -
Most exposed region of HDX Peptide Region 2

| Molecule | Residue | Side chain Exposure | Percent Side Chain Exposure | Critical Functional Amino Acid |
|---|---|---|---|---|
| TL1A_A | T107 | 92.135231 | 0.606153 | |
| TL1A_A | P108 | 122.209305 | 0.814729 | |
| TL1A_A | T109 | 96.343613 | 0.63384 | X ? |
| TL1A_A | Q110 | 124.388191 | 0.654675 | X ? |
| TL1A_A | H111 | 154.51297 | 0.768721 | X * |
| TL1A_A | F112 | 155.469727 | 0.703483 | X * |
| TL1A_A | K113 | 134.771896 | 0.629775 | X * |
| TL1A_A | N114 | 150.291626 | 0.933488 | X ? |
| TL1A_A | Q115 | 124.734985 | 0.6565 | X * |
| TL1A_A | F116 | 86.689079 | 0.392258 | |
| TL1A_A | P117 | 43.018517 | 0.28679 | |
| TL1A_A | A118 | 24.548649 | 0.197973 | |
| TL1A_A | L119 | 0.518295 | 0.002618 | |
| TL1A_A | H120 | 38.194756 | 0.190024 | |

Taken together the structural modeling and HDX data define a discontinuous epitope on the surface of TL1A that is contact with the 10A4 mAb paratope.

Example 10

Tcell Proliferation Assay

A dose response curve of TL1A antibody 10A4.F7.2E8 huIgG4 from 1 µg/ml-0.219 µg/ml was incubated with anti-human CD3 (Biolegend 300314) for 30 min at 37° C., 5% CO2 prior to adding StemCell Kit (19052) enriched CD4+ human T cells. Following 4 days of incubation at 37° C., 5% CO2, 3H-thymidine (0.5 µCi/well) was added for the last 18-20 hr. The plates were harvested onto Unifilter GF/C plates (Packard 5007185) using a Packard Filtermate harvester and allowed to dry. 50 µl/well PerkinElmer Microscint-20 scintillant was added and the plates were counted on a Packard TopCount scintillation counter. EC50 values were calculated by plotting percent of max minus background using GraphPad Prism software.

TABLE 4

Anti-CD3 driven Tcell proliferation
Assay (Hu CD4+ Tcells) (2.45 mg/ml)

| | EC50 [nM] | |
|---|---|---|
| 2.45 mg/ml ELN ref | Donor A | Donor B |
| 99103-061 | 0.211 | 2.2 |
| 99103-067 | 0.328 | 1.2 |
| 99103-072 | 0.295 | 0.318 |
| 99103-078 | 0.242 | 0.196 |
| 99103-079 | 0.277 | 0.341 |
| 99103-090 | 0.323 | 0.329 |

Example 11

Human PBMC IFNg Inhibition Assay (Soluble TL1A Stim)

A dose response curve of TL1A antibody 10A4.F7.2E8 huIgG4 from 3 ug/ml-0.3 ng/ml was incubated with 50 ng/ml human TL1A (in-house) plus 0.25 ng/ml hIL-12 (Peprotech) and 1 ng/ml hIL-18 (R&D Systems), in 96 well round bottom plates with PBMCs isolated from whole human blood. Following an overnight incubation at 37° C., 5% CO2, the supernatants were harvested and IFNg levels were tested with match paired sandwich ELISA antibodies (Thermo Scientific). EC50 values were calculated by plotting percent of max minus background using GraphPad Prism software.

TABLE 5

TL1A + IL-12 + IL-18 driven IFNg (Hu PBMCs) (2.45 mg/ml)

| | EC50 [nM] | |
|---|---|---|
| 2.45 mg/ml ELN ref | Donor A | Donor B |
| 97305-032 | 0.131 | 0.197 |
| 97305-037 | 0.138 | 0.289 |
| 97305-040 | 0.167 | 0.146 |
| 97305-041 | 0.209 | 0.283 |
| 97305-044 | 0.272 | 0.211 |
| 97305-047 | 0.095 | 0.185 |
| 97305-050 | 0.209 | 0.163 |
| 97305-061 | 0.26 | 0.152 |
| 99932-005481 | 0.301 | 0.196 |

TABLE 6

TL1A + IL-12 + IL-18 driven IFNg (Hu PBMCs) (5.9 mg/ml)

| | EC50 [nM] | |
|---|---|---|
| 5.9 mg/ml ELN ref | Donor A | Donor B |
| 99932-005481 | 0.295 | 0.241 |

Example 12

Human PBMC IFNg Inhibition Assay (TL1A Expressing CHOs Cells Stim)

A dose response curve of TL1A antibody 10A4.F7.2E8 huIgG4 from 3 ug/ml-0.3 ng/ml was incubated with irradiated TL1A expressing CHOs cells plus 0.25 ng/ml hIL-12 (Peprotech) and 1 ng/ml hIL-18 (R&D Systems), in 96 well round bottom plates with PBMCs isolated from whole human blood. Following an overnight incubation at 37° C., 5% CO2, the supernatants were harvested and IFNg levels were tested with match paired sandwich ELISA antibodies (Thermo Scientific). EC50 values were calculated by plotting percent of max minus background using GraphPad Prism software.

TABLE 7

TL1A-expressing CHO cells + IL-12 + IL-18 driven IFNg (Hu PBMCs)(2.45 mg/ml)

| 2.45 mg/ml ELN ref | EC50 [nM] | |
|---|---|---|
| | Donor A | Donor B |
| 97305-034 | 0.234 | 0.214 |

Example 13

Human Tcell IFNg Inhibition Assay

A dose response curve of TL1A antibody 10A4.F7.2E8 huIgG4 from 3 ug/ml-0.3 ng/ml was incubated with 50 ng/ml human TL1A (in-house) plus 0.5 ng/ml hIL-12 (Peprotech) and 5 ng/ml hIL-18 (R&D Systems), in 96 well round bottom plates with Stem Cell (19051) enriched human T cells. Following an overnight incubation at 37° C., 5% CO2, the supernatants were harvested and IFNg levels were tested with match paired sandwich ELISA antibodies (Thermo Scientific). EC50 values were calculated by plotting percent of max minus background using GraphPad Prism software.

TABLE 8

TL1A + IL-12 + IL-18 driven IFNg (Hu Tcells) (2.45 mg/ml)

| 2.45 mg/ml ELN ref | EC50 [nM] | |
|---|---|---|
| | Donor A | Donor B |
| 97305-062 | 0.18 | 0.259 |
| 97305-064 | 0.235 | 0.199 |
| 97305-066 | 0.331 | 0.347 |
| 97305-077 | 0.241 | 0.258 |
| 97305-082 | 0.034 | 0.039 |
| 99932-003797 | 0.355 | 0.312 |
| 99932-004083 | 0.393 | 0.311 |
| 99932-004084 | 0.367 | 0.303 |
| 99932-004439 | 0.185 | 0.194 |
| 99932-004774 | 0.22 | 0.319 |
| 99932-004955 | 0.172 | 0.211 |

TABLE 9

TL1A + IL-12 + IL-18 driven IFNg (Hu Tcells) (5.9 mg/ml)

| 5.9 mg/ml ELN ref | EC50 [nM] | |
|---|---|---|
| | Donor A | Donor B |
| 99932-004774 | 0.171 | 0.243 |
| 99932-004955 | 0.273 | 0.182 |

TABLE 10

TL1A + IL-12 + IL-18 driven IFNg (Hu Tcells) (4.8 mg/ml)

| 4.8 mg/ml ELN ref | EC50 [nM] | |
|---|---|---|
| | Donor A | Donor B |
| 97305-082 | 0.162 | 0.143 |
| 99932-003797 | 0.303 | 0.361 |
| 99932-004083 | 0.27 | — |
| 99932-004084 | 0.316 | 0.345 |
| 99932-004439 | 0.262 | 0.157 |
| 99932-004774 | 0.177 | 0.267 |
| 99932-004955 | 0.193 | 0.287 |
| 99932-005751 | 0.216 | 0.138 |

Example 14

Human NK Cell IFNg Inhibition Assay

A dose response curve of TL1A antibody 10A4.F7.2E8 huIgG4 from 3 ug/ml-0.3 ng/ml was incubated with 50 ng/ml human TL1A (in-house) plus 0.5 ng/ml hIL-12 (Peprotech) and 1 ng/ml hIL-18 (R&D Systems), in 96 well round bottom plates with Stem Cell (19055) enriched human NK cells. Following an overnight incubation at 37° C., 5% CO2, the supernatants were harvested and IFNg levels were tested with match paired sandwich ELISA antibodies (Thermo Scientific). EC50 values were calculated by plotting percent of max minus background using GraphPad Prism software.

TABLE 11

TL1A + IL-12 + IL-18 driven IFNg (Hu NKcells)(2.45 mg/ml)

| 2.45 mg/ml ELN ref | EC50 [nM] | |
|---|---|---|
| | Donor A | Donor B |
| 97305-070 | 0.16 | 0.253 |
| 97305-075 | 0.147 | 0.162 |

Example 15

Human Whole Blood IFNg Inhibition Assay

A dose response curve of TL1A antibody 10A4.F7.2E8 huIgG4 from 3 ug/ml-0.3 ng/ml was incubated with 50 ng/ml human TL1A (in-house) plus 0.5 ng/ml hIL-12 (Peprotech) and 5 ng/ml hIL-18 (R&D Systems), in 96 well round bottom plates with heparin treated whole human blood. Following an overnight incubation at 37° C., 5% CO2, the plates were centrifuged at 1900 rpm for 10 min, the plasma was harvested and IFNg levels were tested with match paired sandwich ELISA antibodies (Thermo Scientific). EC50 values were calculated by plotting percent of max minus background using GraphPad Prism software.

TABLE 12

TL1A + IL-12 + IL-18 driven IFNg (Hu WB)(2.45 mg/ml)

| 2.45 mg/ml ELN ref | EC50 [nM] Donor A | Donor B |
|---|---|---|
| 97305-029 | 0.32 | 0.54 |
| 97305-033 | 0.284 | 0.108 |

Example 16

Cynomolgus PBMC IFNg Inhibition Assay

A dose response curve of TL1A antibody 10A4.F7.2E8 huIgG4 from 3 ug/ml-0.3 ng/ml was incubated with 50 ng/ml cynomolgus TL1A (in-house) plus 2 ng/ml hIL-12 (Peprotech) and 5 ng/ml hIL-18 (R&D Systems), in 96 well round bottom plates with PBMCs isolated from whole cynomolgus blood. Following an overnight incubation at 37° C., 5% CO2, the supernatants were harvested and IFNg levels were tested with a primate ELISA kit (R&D Systems). EC50 values were calculated by plotting percent of max minus background using GraphPad Prism software.

TABLE 13

TL1A + IL-12 + IL-18 driven IFNg (Cyno PBMCs)(2.45 mg · ml)

| 2.45 mg/ml ELN ref | EC50 [nM] Donor A | Donor B |
|---|---|---|
| 97305-067 | 0.122 | 0.164 |
| 97305-071 | 0.154 | 0.133 |

TABLE 13-continued

TL1A + IL-12 + IL-18 driven IFNg (Cyno PBMCs)(2.45 mg · ml)

| 2.45 mg/ml ELN ref | EC50 [nM] Donor A | Donor B |
|---|---|---|
| 97305-074 | 0.105 | 0.129 |
| 97305-076 | 0.097 | 0.093 |

Example 17

Human pNFkB Inhibition Assay

A dose response curve of TL1A antibody 10A4.F7.2E8 huIgG4 was incubated with 0.5 ug/ml human TL1A (in-house) for 15 minutes at 37° C.; 5% CO2 with heparin treated whole human blood in 96-well deep-well plates. Following the stimulation the cells were lysed/fixed, permeabilized, and stained with the appropriate panel of antibodies. Measurements were performed on a flow cytometer and the analysis was performed on TreeStar's FlowJo analysis software. EC50 values were calculated using GraphPad Prism software.

TABLE 14

TL1A-driven phospho-NFkB in Hu Whole Blood(2.45 mg/ml)

| 2.45 mg/ml ELN ref | EC50 [nM] Donor A | Donor B | Cell Type |
|---|---|---|---|
| A010F-003 | 2.64 | 2.94 | CD4+ T-cells |
| A010F-007 | 0.770 | 3.240 | CD4+ T-cells |
|  | 0.850 | N/A | CD8+ T-cells |
|  | 0.830 | N/A | CD3+CD4−CD8− T-cells |

The invention claimed is:

1. An antibody, or antigen binding fragment thereof, that binds to human TL1A (TNF-like ligand 1A) and comprises:
   a) a heavy chain variable domain comprising:
      CDRH1 comprising the sequence of SEQ ID NO:7;
      CDRH2 comprising the sequence of SEQ ID NO:8; and
      CDRH3 comprising the sequence of SEQ ID NO:9; and
   b) a light chain variable domain comprising:
      CDRL1 comprising the sequence of SEQ ID NO:12;
      CDRL2 comprising the sequence of SEQ ID NO:13; and
      CDRL3 comprising the sequence of SEQ ID NO:14;
   wherein the antibody or fragment inhibits the binding of human TL1A to DR3.

2. The antibody, or antigen binding fragment of claim 1 that binds to TL1A (SEQ ID NO:20) at an epitope comprising one or more of residues 102-116(SEQ ID NO:16) or 166-180(SEQ ID NO: 17).

3. The antibody or antigen binding fragment of claim 2 that binds to TL1A at an epitope comprising one or more of residues $^{169}$QAGR$^{172}$ (SEQ ID NO:21) and one or more of residues $^{113}$KNQF$^{116}$ (SEQ ID NO:22).

4. The antibody or antigen binding fragment of claim 2 that binds to TL1A at an epitope comprising the sequence $^{169}$QAGR$^{172}$ (SEQ ID NO:21) and/or $^{113}$KNQF$^{116}$ (SEQ ID NO:22).

5. The antibody or antigen binding fragment of claim 1 wherein the antibody binds to both human and cynomolgus TL1A.

6. The antibody or antigen binding fragment of claim 1 comprising one or more heavy chains and one or more light chains, wherein:
   a) the heavy chain comprises a heavy chain variable region having at least 80% sequence identity with the sequence of SEQ ID NO: 6; and
   a) the light chain comprises a light chain variable region having at least 80% sequence identity with the sequence of SEQ ID NO: 11.

7. The antibody of claim 1, wherein the antibody is a human IgG1 Fc variant with reduced or eliminated effector function.

8. A nucleic acid encoding the heavy and light chain variable region of the antibody of antigen binding fragment of claim 1.

9. An expression vector comprising the nucleic acid molecule of claim 8.

10. A host cell transformed with an expression vector of claim 9.

11. A method of producing an anti-TL1A antibody or antigen binding fragment thereof comprising culturing the host cell of claim 10 under conditions that allows production of the antibody or fragment, and purifying the antibody from the cell.

12. A method of detecting the presence of TL1A in a sample comprising contacting the sample with the antibody, or antigen binding fragment thereof, of claim 1 under conditions that allow for formation of a complex between the antibody, or antigen binding fragment thereof, and TL1A, and detecting the formation of the complex.

* * * * *

SEQUENCE LISTING

```
<160> NUMBER OF SEQ ID NOS: 25

<210> SEQ ID NO 1
<211> LENGTH: 645
<212> TYPE: DNA
<213> ORGANISM: Homo sapiens

<400> SEQUENCE: 1
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctctcac tttcggcgga     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 2
<211> LENGTH: 214
<212> TYPE: PRT
<213> ORGANISM: Homo sapiens

<400> SEQUENCE: 2

| Ala | Ile | Gln | Leu | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Ser | Ser | Ala |
| | | 20 | | | | | 25 | | | | | 30 | | | |

| Leu | Ala | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Asp | Ala | Ser | Ser | Leu | Glu | Ser | Gly | Val | Pro | Ser | Arg | Phe | Ser | Gly |
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Gln | Gln | Phe | Asn | Ser | Tyr | Pro | Leu |
| | | | | 85 | | | | | 90 | | | | | 95 | |

| Thr | Phe | Gly | Gly | Gly | Thr | Lys | Val | Glu | Ile | Lys | Arg | Thr | Val | Ala | Ala |
| | | | 100 | | | | | 105 | | | | | 110 | | |

| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |

| Thr | Ala | Ser | Val | Val | Cys | Leu | Leu | Asn | Asn | Phe | Tyr | Pro | Arg | Glu | Ala |
| | 130 | | | | | 135 | | | | | 140 | | | | |

| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |

| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |

| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |

| Ala | Cys | Glu | Val | Thr | His | Gln | Gly | Leu | Ser | Ser | Pro | Val | Thr | Lys | Ser |
| | | | 195 | | | | | 200 | | | | | 205 | | |

| Phe | Asn | Arg | Gly | Glu | Cys |
| | 210 | | | | |

<210> SEQ ID NO 3
<211> LENGTH: 1347
<212> TYPE: DNA
<213> ORGANISM: Homo sapiens

<400> SEQUENCE: 3

| | |
|---|---|
| cagctgcagc tgcaggagtc gggcccagga ctggtgaagc cttcggagac cctgtccctc | 60 |
| acctgcactg tctctggtgg ctccatcagc agtaggagtt actactgggg ctggatccgc | 120 |
| cagcccccag ggaagggact ggagtggatt ggagtatct attataatgg gagaacctac | 180 |
| tacaacccgt ccctcaagag tcgagtcacc atatccgtag acacgtccaa gaaccagttc | 240 |
| tccctgaagc tgagctctgt gaccgccgca gacacggctg tgtattactg tgcgagggag | 300 |
| gactacggtg actacggagc ttttgatatc tggggccaag ggacaatggt caccgtctct | 360 |
| tcagctagca ccaagggccc atccgtcttc cccctggcgc cctgctccag gagcacctcc | 420 |
| gagagcacag ccgccctggg ctgcctggtc aaggactact ccccgaacc ggtgacggtg | 480 |
| tcgtggaact caggcgccct gaccagcggc gtgcacacct tccggctgt cctacagtcc | 540 |
| tcaggactct actccctcag cagcgtggtg accgtgccct ccagcagctt gggcacgaag | 600 |

```
acctacacct gcaacgtaga tcacaagccc agcaacacca aggtggacaa gagagttgag     660
tccaaatatg gtcccccatg ccaccatgc ccagcacctg agttcctggg gggaccatca      720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctaaccgtgg acaagagcag gtggcaggag    1260
gggaatgtct tctcatgctc cgtgatgcat gaggctctgc acaaccacta cacacagaag    1320
agcctctccc tgtctctggg taaatga                                        1347
```

<210> SEQ ID NO 4
<211> LENGTH: 448
<212> TYPE: PRT
<213> ORGANISM: Homo sapiens
<400> SEQUENCE: 4

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asn Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Tyr Gly Asp Tyr Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240
```

```
Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 5
<211> LENGTH: 363
<212> TYPE: DNA
<213> ORGANISM: Homo sapiens

<400> SEQUENCE: 5
cagctgcagc tgcaggagtc gggcccagga ctggtgaagc cttcggagac cctgtccctc    60
acctgcactg tctctggtgg ctccatcagc agtaggagtt actactgggg ctggatccgc   120 cagccccag ggaagggact ggagtggatt gggagtatct attataatgg gagaacctac    180
tacaacccgt ccctcaagag tcgagtcacc atatccgtag acacgtccaa gaaccagttc   240
tccctgaagc tgagctctgt gaccgccgca gacacggctg tgtattactg cgagggag    300 gactacggtg actacggagc ttttgatatc tggggccaag ggacaatggt caccgtctct   360
tca                                                                  363

<210> SEQ ID NO 6
<211> LENGTH: 121
<212> TYPE: PRT
<213> ORGANISM: Homo sapiens

<400> SEQUENCE: 6

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asn Gly Arg Thr Tyr Tyr Asn Pro Ser
```

```
                      50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Asp Tyr Gly Asp Tyr Gly Ala Phe Asp Ile Trp Gly
            100                 105                 110

Gln Gly Thr Met Val Thr Val Ser Ser
        115                 120

<210> SEQ ID NO 7
<211> LENGTH: 7
<212> TYPE: PRT
<213> ORGANISM: Homo sapiens

<400> SEQUENCE: 7

Ser Arg Ser Tyr Tyr Trp Gly
1               5

<210> SEQ ID NO 8
<211> LENGTH: 16
<212> TYPE: PRT
<213> ORGANISM: Homo sapiens

<400> SEQUENCE: 8

Ser Ile Tyr Tyr Asn Gly Arg Thr Tyr Tyr Asn Pro Ser Leu Lys Ser
1               5                   10                  15

<210> SEQ ID NO 9
<211> LENGTH: 11
<212> TYPE: PRT
<213> ORGANISM: Homo sapiens

<400> SEQUENCE: 9

Glu Asp Tyr Gly Asp Tyr Gly Ala Phe Asp Ile
1               5                   10

<210> SEQ ID NO 10
<211> LENGTH: 321
<212> TYPE: DNA
<213> ORGANISM: Homo sapiens

<400> SEQUENCE: 10
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctctcac tttcggcgga     300
gggaccaagg tggagatcaa a                                              321

<210> SEQ ID NO 11
<211> LENGTH: 107
<212> TYPE: PRT
<213> ORGANISM: Homo sapiens

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
```

```
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Leu
                85                  90                  95
Thr Phe Gly Gly Gly Thr Lys Val Glu Ile Lys
            100                 105

<210> SEQ ID NO 12
<211> LENGTH: 11
<212> TYPE: PRT
<213> ORGANISM: Homo sapiens

<400> SEQUENCE: 12

Arg Ala Ser Gln Gly Ile Ser Ser Ala Leu Ala
1               5                   10

<210> SEQ ID NO 13
<211> LENGTH: 7
<212> TYPE: PRT
<213> ORGANISM: Homo sapiens

<400> SEQUENCE: 13

Asp Ala Ser Ser Leu Glu Ser
1               5

<210> SEQ ID NO 14
<211> LENGTH: 9
<212> TYPE: PRT
<213> ORGANISM: Homo sapiens

<400> SEQUENCE: 14

Gln Gln Phe Asn Ser Tyr Pro Leu Thr
1               5

<210> SEQ ID NO 15
<211> LENGTH: 17
<212> TYPE: PRT
<213> ORGANISM: Homo sapiens

<400> SEQUENCE: 15

Gln Val Tyr Ala Pro Leu Arg Ala Asp Gly Asp Lys Pro Arg Ala His
1               5                   10                  15
Leu

<210> SEQ ID NO 16
<211> LENGTH: 15
<212> TYPE: PRT
<213> ORGANISM: Homo sapiens

<400> SEQUENCE: 16

Thr Val Val Arg Gln Thr Pro Thr Gln His Phe Lys Asn Gln Phe
1               5                   10                  15

<210> SEQ ID NO 17
<211> LENGTH: 15
<212> TYPE: PRT
<213> ORGANISM: Homo sapiens
```

```
<400> SEQUENCE: 17

Glu Ile Arg Gln Ala Gly Arg Pro Asn Lys Pro Asp Ser Ile Thr
1               5                   10                  15

<210> SEQ ID NO 18
<211> LENGTH: 13
<212> TYPE: PRT
<213> ORGANISM: Homo sapiens

<400> SEQUENCE: 18

Gln Ala Leu Lys Gly Gln Glu Phe Ala Pro Ser His Gln
1               5                   10

<210> SEQ ID NO 19
<211> LENGTH: 251
<212> TYPE: PRT
<213> ORGANISM: Homo sapiens

<400> SEQUENCE: 19

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 20
<211> LENGTH: 253
<212> TYPE: PRT
<213> ORGANISM: Homo sapiens
```

<400> SEQUENCE: 20

```
Thr Ser Gly Ser Ser His His His His His Ser Ser Gly Ile Glu
1               5                   10                  15

Gly Arg Gly Ser His Met Gly Asp Arg Met Lys Gln Ile Glu Asp Lys
            20                  25                  30

Ile Glu Glu Ile Leu Ser Lys Ile Tyr His Ile Glu Asn Glu Ile Ala
            35                  40                  45

Arg Ile Lys Lys Leu Ile Gly Glu Arg Ala Ser Gln Leu Arg Ala Gln
        50                  55                  60

Gly Glu Ala Cys Val Gln Phe Gln Ala Leu Lys Gly Gln Glu Phe Ala
65                  70                  75                  80

Pro Ser His Gln Gln Val Tyr Ala Pro Leu Arg Ala Asp Gly Asp Lys
            85                  90                  95

Pro Arg Ala His Leu Thr Val Val Arg Gln Thr Pro Thr Gln His Phe
            100                 105                 110

Lys Asn Gln Phe Pro Ala Leu His Trp Glu His Glu Leu Gly Leu Ala
            115                 120                 125

Phe Thr Lys Asn Arg Met Asn Tyr Thr Asn Lys Phe Leu Leu Ile Pro
130                 135                 140

Glu Ser Gly Asp Tyr Phe Ile Tyr Ser Gln Val Thr Phe Arg Gly Met
145                 150                 155                 160

Thr Ser Glu Cys Ser Glu Ile Arg Gln Ala Gly Arg Pro Asn Lys Pro
            165                 170                 175

Asp Ser Ile Thr Val Val Ile Thr Lys Val Thr Asp Ser Tyr Pro Glu
            180                 185                 190

Pro Thr Gln Leu Leu Met Gly Thr Lys Ser Val Cys Glu Val Gly Ser
            195                 200                 205

Asn Trp Phe Gln Pro Ile Tyr Leu Gly Ala Met Phe Ser Leu Gln Glu
            210                 215                 220

Gly Asp Lys Leu Met Val Asn Val Ser Asp Ile Ser Leu Val Asp Tyr
225                 230                 235                 240

Thr Lys Glu Asp Lys Thr Phe Phe Gly Ala Phe Leu Leu
            245                 250
```

<210> SEQ ID NO 21
<211> LENGTH: 4
<212> TYPE: PRT
<213> ORGANISM: Homo sapiens

<400> SEQUENCE: 21

```
Gln Ala Gly Arg
1
```

<210> SEQ ID NO 22
<211> LENGTH: 4
<212> TYPE: PRT
<213> ORGANISM: Homo sapiens

<400> SEQUENCE: 22

```
Lys Asn Gln Phe
1
```

<210> SEQ ID NO 23
<211> LENGTH: 19
<212> TYPE: PRT
<213> ORGANISM: Homo sapiens

<400> SEQUENCE: 23

```
Ser Cys Ser Glu Ile Arg Gln Ala Gly Arg Pro Asn Lys Pro Asp
1               5                   10                  15

Ser Ile Thr

<210> SEQ ID NO 24
<211> LENGTH: 15
<212> TYPE: PRT
<213> ORGANISM: Homo sapiens

<400> SEQUENCE: 24

Glu Ile Arg Gln Ala Gly Arg Pro Asn Lys Pro Asp Ser Ile Thr
1               5                   10                  15

<210> SEQ ID NO 25
<211> LENGTH: 14
<212> TYPE: PRT
<213> ORGANISM: Homo sapiens

<400> SEQUENCE: 25

Thr Pro Thr Gln His Phe Lys Asn Gln Phe Pro Ala Leu His
1               5                   10
```